US012703688B1

(12) United States Patent
Parsons

(10) Patent No.: US 12,703,688 B1
(45) Date of Patent: Aug. 11, 2026

(54) CRYSTALLINE FORM, AND PROCESS FOR ITS PRODUCTION

(71) Applicant: Alterity Therapeutics Limited, Melbourne (AU)

(72) Inventor: Jack Gordon Parsons, Melbourne (AU)

(73) Assignee: Alterity Therapeutics Limited, Melbourne (AU)

( * ) Notice: Subject to any disclaimer, the term of this patent is extended or adjusted under 35 U.S.C. 154(b) by 0 days.

(21) Appl. No.: 19/296,290

(22) Filed: Aug. 11, 2025

(30) Foreign Application Priority Data

Mar. 14, 2025 (AU) ................................ 2025900806

(51) Int. Cl.
*C07D 239/90* (2006.01)
*A61K 31/517* (2006.01)
*C07C 309/04* (2006.01)

(52) U.S. Cl.
CPC .......... *C07D 239/90* (2013.01); *A61K 31/517* (2013.01); *C07C 309/04* (2013.01); *C07B 2200/13* (2013.01)

(58) Field of Classification Search
None
See application file for complete search history.

(56) References Cited

U.S. PATENT DOCUMENTS 8,889,695 B2 11/2014 Huggins et al.
2014/0294724 A1 10/2014 Chain

FOREIGN PATENT DOCUMENTS

| | | | |
|---|---|---|---|
| WO | 2004/031161 | A1 | 4/2004 |
| WO | 2005/095360 | A1 | 10/2005 |
| WO | 2010071944 | A1 | 7/2010 |
| WO | 2013063086 | A1 | 5/2013 |
| WO | 2024228599 | A1 | 11/2024 |
| WO | 2025006917 | A1 | 1/2025 |
| WO | 2025059726 | A1 | 3/2025 |
| WO | 2026011229 | A1 | 1/2026 |

OTHER PUBLICATIONS

Clinical trial notification; "A Phase 1 clinical trial to assess the safety, tolerability and pharmacokinetics of PBT434 in healthy volunteers;" Reg. No. ACTRN12618000541202; Jan. 18, 2019; https://www.anzctr.org.au/Trial/Registration/TrialReview.aspx?id=374741&isReview=true.

Clinical trial notification; "A Phase 1 Study to Evaluate a Tablet Formulation of PBT434 in Healthy Volunteers;" Reg. No. ACTRN12620001244998; Nov. 20, 2020; www.anzotr.org.au/Trial/Registration/TrialReview.aspx?id=380631&isReview=true.

Clinical trial notification; "Study of ATH434 in Participants with Multiple System Atrophy;" Reg. No. NCT05109091; Nov. 5, 2021; https://www.anzotr.org.au/Trial/Registration/TrialReview.aspx?id=20539&isClinicalTrial=True.

Clinical trial notification; "Study of ATH434 in Participants with Multiple System Atrophy;" ClinicalTrials.gov ID NCT05109091; Dec. 13, 2024; https:clinicaltrials.gov/study/NCT06109091.

Clinical trial notification; "Study of ATH434 in Participants with Multiple System Atrophy;" Identifiers NCT05109091, ATH434-201; Nov. 28, 2024; https://ctv.veeva.com/study/study-of-ath434-in-participants-with-multiple-system-atrophy.

Clinical trial notification; "Study of ATH434 in Participants With Multiple System Atrophy;" Health Research Authority; IRAS ID 1004373; Apr. 8, 2022; https://www.hra.nhs.uk/planning-and-improving-research/application-summanes/research-summaries/study-of-ath434-in-participants-with-multiple-system-atrophy/.

Lemos et al.; "Current experimental disease-modifying therapeutics for multiple system atrophy;" Journal of Neural Transmission (2021) 128:1529-1543; Aug. 16, 2021; https://doi.org/10.1007/s00702-021-02406-z.

Pall et al.; "ATH434, a promising iron-targeting compound for treating iron regulation disorders;" Metallomics, 16, 2024, mfae044; Sep. 24, 2024; https://doi.org/10.1093/mtomcs/mfae044.

Pipeline—Alterity Therapeutics; https://alteritvtherapeutics.com/pipeline/S.

Stamler et al.; "Topline Data from a Randomized, Double Blind, Placebo Controlled Phase 2 Study of ATH434 in Multiple System Atrophy (S37.008);" Neurology AAN Publications; Apr. 8, 2025 issue 104(7_Supplement_1); https://www.neurology.org/doi/10.1212/WNL.0000000000212526.

Claassen et al; "Topline Data from a Randomized, Double Blind, Placebo Controlled Phase 2 Study of ATH434 in Multiple System Atrophy;" Presentation S37-Movement Disorders: Clinical Trials; Poster/Presentation No. 8; Apr. 9, 2025; https://www.aan.com/msa/Public/Events/AbstractDetails/58512.

Stamler et al.; "A Phase 1 Study of PBT434, a Novel Small Molecule Inhibitor of α-Synuclein Aggregation, in Adult and Older Adult Volunteers (4871);"Neurology AAN Publications; Apr. 14, 2020 issue 94(15_supplement); https://www.neurology.org/do:/10.1212/WNL94.15_supplement.4871#:~:text=Results%3A,102.5%20to%20229.5%20ng%.

Stamler et al.; "A First in Human Study of PBT434, a Novel Small Molecule Inhibitor of α-Synuclein Aggregation;" American Academy of Neurology—S4.001; May 5, 2019; https://www.neurology.org/doi/10.1212/WNL.92.15_supplement.S4.001.

(Continued)

*Primary Examiner* — Juliet C Switzer
*Assistant Examiner* — Dawanna Shar-Day White
(74) *Attorney, Agent, or Firm* — Kilpatrick Townsend & Stockton LLP

(57) ABSTRACT

Provided herein is a crystalline form (Form A) of a salt of a compound of formula (I) as defined herein. The present disclosure also relates to processes for the production of Form A of the salt, and to pharmaceutical compositions and therapeutic methods involving the salt and crystalline Form A.

21 Claims, 7 Drawing Sheets

(56) References Cited

OTHER PUBLICATIONS

Manufacturing Services Agreement for PBT434 Supply between Prana Biotechnology Ltd and Dr. Reddy's Laboratories Limited; Mar. 28, 2014; https://www.sec.gov/Archives/edgar/data/1131343/000117891314003317/exhibit 4-36.htm.
Stamler et al.; "ATH434 Slowed Disease Progression in a Phase 2 Study in Multiple System Atrophy;" Alterity Therapeutics, Vanderbilt University Medical Center; Poster No. 85, International MSA Congress, 2025, Boston, MA; https://alteritytherapeutics.com/wp-content/uploads/the-science/msa-2025-poster-stamler-201tid.pdf.
Stamler et al.; "A Randomized, Double Blind, Placebo Controlled Phase 2 Study of ATH434 in Multiple System Atrophy;" Vanderbilt University Medical Center, Alterity Therapeutics; International MSA Congress, Boston, MA; May 9, 2025; https://alteritytherapeutics.com/wp-content/uploads/a-randomized-double-blind-placebo-controlled-phase-2-study-of-ath434-in-msa-1.pdf.
Stamler et al.; "Topline data from a Randomized, Double Blind, Placebo Controlled Phase 2 Study of ATH434 in MSA;" Vanderbilt University Medical Center, Alterity Therapeutics; American Academy of Neurology Annual Meeting 2025 (San Diego); https://alleritytherapeutics.com/wp-content/uploads/the-science/aan-2025_ath434-201_oral-presentation.pdf.
Bailey et al.; "Potent Antioxidant and Mitochondrial-protective Effects of ATH434, a Novel Therapeutic with Moderate Iron-binding Affinity;" University at Buffalo, Department of Biochemistry Jacobs School of Medicine and Biomedical Sciences; Oct. 10, 2024; https://alteritytherapeutics.com/wp-content/uploads/DB-sin-2024-poster-10Oct24.pdf.
Claassen et al.; "Preliminary Efficacy and Safety of ATH434 in Multiple System Atrophy;" Alterity Therapeutics, Vanderbilt University Medical Center; International Congress of Parkinson's Diseases and Movement Disorders; 2024; https://alteritytherapeutics.com/wp-content/uploads/poster-MDS-2024-Claassen-202.pdf.
Stamler et al.; "A Phase 2 study of ATH434, a Novel Inhibitor of a-synuclein Aggregation, for the Treatment of Multiple System Atrophy;" Alterity Therapeutics, Vanderbilt University Medical Center; Abstract No. 4; International Congress of Parkinson's Disease and Movement Disorders; 2024; Philadelphia, PA; https://alteritytherapeutics.com/wp-content/uploads/poster-MDS-2024-Stamler-201.pdf.
Bradbury et al.; "Effects of ATH434, a Clinical-Phase Small Molecule with Moderate Affinity for Iron, in Hemiparkinsonian Macaques;" Alterity Therapeutics, Movement Disorders Society; Sep. 27-Oct. 1, 2024; Abstract No. 803; https://alleritytherapeutics.com/wp-content/uploads/poster-MDS-2024-Bradbury-MPTP.pdf.
Pall et al.; "Biophysical Characteristics of ATH434, a Unique Iron-Targeting Drug for Treating Friedreich's Ataxia;" Department of Pharmaceutical Sciences, Wayne State University; Alterity Therapeutics; 2024; https://alteritytherapeutics.com/wp-content/uploads/Biophysical-Characteristics-of-ATH434_Unique-iron-targeting-drug-for-treating-Friedreichs-Ataxia.pdf.
Stamler et al.; "A Phase 2 study of ATH434, a Novel Inhibitor of a-synuclein Aggregation, for the Treatment of Multiple System Atrophy;" Alterity Therapeutics; Vanderbilt University Medical Center; American Academy of Neurology; Apr. 13-18, 2024; Abstract No. 6631; https://alteritytherapeutics.com/wp-content/uploads/poster.Stamler-AAN-2024-P2-Baseline.pdf.
Bradbury et al.; "Effects of ATH434, a Clinical-Phase Small Molecule with Moderate Affinity for Iron, in Hemiparkinsonian Macaques;" Alterity Therapeutics; The Florey Institute of Neuroscience and Mental health; Vanderbilt University Medical School; Future of Parkinson's Disease Conference; Dec. 1, 2023; Austin, Texas; https://alteritytherapeutics.com/wp-content/uploads/Effects-of-ATH434_Dec02-2023.pdf.
Bailey et al.; "Potent antioxidant and Mitochondrial-protect Effects of ATH434, a Novel Inhibitor of a-Synuclein Aggregation with Moderate Iron-binding Affinity;" Department of Biochemistry, SUNY University at Buffalo; Alterity Therapeutics; 2023; https://alteritytherapeutics.com/wp-content/uploads/DB-SIN-2023-poster-for-PR_v2.pdf.
Beauchamp et al.; "ATH434 Rescues Pre-motor Hyposmia in a Mouse Model of Parkinsonism;" Neurotherapeutics; vol. 19; pp. 1966-1975; Sep. 29, 2022; https://link.springer.com/article/10.1007/13311-022-01300-0.
Finkelstein et al.; "The Compound ATH434 Prevents Alpha-Synuclein Toxicity in a Murine Model of Multiple System Atrophy;" Journal of Parkinson's Disease 12 (2022) 105-115; DOI 10.3233/JPD-212877; Oct. 30, 2021.
Diwakarla et al.; "ATH434 Reverses Colorectal Dysfunction in the A53T Mouse Model of Parkinson's Disease;" Journal of Parkinson's Disease 11 (2021) 1821-1832; DOI 10.3233/JPD-212731; Aug. 4, 2021.
Heras-Garvin et al.; "ATH434 Reduces $\alpha$-Synuclein-Related Neurodegeneration in a Murine Model of Multiple System Atrophy;" Movement Disorders; (wileyonlinelibrary.com). DOI: 10.1002/mds.28714; Jun. 14, 2021.
Heras-Garvin et al.; "ATH434 Preserves Dopaminergic Neurons, Reduces a-synuclein Oligomerization, and Improves Motor Function in a Transgenic Murine Multiple System Atrophy Model (1842);" Neurology AAN Publications; 96 (15_supplement); Apr. 13, 2021; https://doi.org/10.1212/WNL.96.15_supplement.1842.
Alterity Therapeutics Announces Presentation of ATH434 at the American Autonomic Society Virtual Meeting 2021; Nov. 9, 2021.
Stamler et al.; "Cardiovascular safety and pharmacokinetics of ATH434, a novel small molecule inhibitor of $\alpha$-synuclein aggregation, in adults and older adults;" American Autonomic Society Virtual Meeting; Poster No. 84; Nov. 4-6, 2021.
Stamler et al.; "A First in Human Study of PBT434, a Novel Small Molecule Inhibitor of $\alpha$-Synuclein Aggregation (S4.001);" Neurology AAN Publication; Apr. 9, 2019 issue; 92(15_supplement); https://doi.org/10.1212/WNL.92.15_supplement.S4.001.
Stamler et al.; "A First in Human Study of PBT434, a Novel Small Molecule Inhibitor of Alpha-Synuclein Aggregation;" Abstract No. 1093; 2019 International Congress; Sep. 24, 2019; https://www.nidsabstracts.org/abstract/a-first-in-human-study-of-pbt434-a-novel-small-molecule-inhibi itor-of-alpha-synuclein-aggregation/.
Finkelstein et al.; "PBT434 prevents the accumulation of glial cell inclusions and insoluble alpha-synuclein in a mouse model of Multiple System Atrophy;" Abstract No. 990; 2018 International Congress; Oct. 7, 2018; https://www.mdsabstracts.org/abstract/pbt434-prevents-the-accumulation-of-glial-cell-inclusions-and-insoluble-alpha-synuclein-in-a-mouse-model-of-multiple-system-atrophy/.
Finkelstein et al.; "The novel compound PBT434 prevents iron mediated neurodegeneration and alpha-synuclein toxicity in multiple models of Parkinson's disease;" Acta Neuropathologica Communications; (2017) 5:53; DOI 10.1186/s40478-017-0456-2; Jun. 28, 2017; https://actaneurocommis.biomedcentral.com/articles/10.1186/s40478-017-0456-2.
Bond et al.; "ATH434, an iron chaperone for neurodegenerative diseases;" AusIron 2024; Nov. 18-19, 2024.
Announcement: Presentation on ATH434 to American Academy of Neurology. May 21, 2020. https://alteritytx.com/announcements/3651222.
Announcement: New data independently confirms safety profile of ATH343. Aug. 4, 2020. https://alteritytx.com/announcements/3599617.
Announcement: ATH434 protects brain cells and improves motor function. Apr. 21, 2021. https://alteritytx.com/announcements/3960628.
Announcement: EU Regulatory Guidance for ATH434 Phase 2 Clinical Trial. Jun. 23, 2021. https://alteritytx.com/announcements/3983368.
Announcement: Alterity Therapeutics Announces Publication of Data Demonstrating ATH434 is Neuroprotective and Improves Motor Function. Jul. 15, 2021. https://alteritytx.com/announcements/3992744.
Announcement. Alterity Therapeutics Announces Expanded ATH434 Phase 2 Clinical Development Program. Oct. 19, 2021. https://alteritytx.com/announcements/4036712.

(56) References Cited

OTHER PUBLICATIONS

Announcement: New Data Advance ATH434 as Neurodegeneration treatment. Nov. 4, 2021. https://alteritytx.com/announcements/4047039.
Announcement: Alterity Therapeutics Launches ATH434 Phase 2 Clinical Trial for the Treatment of Patients with Multiple System Atrophy. https://www.prnewswire.com/news-releases/alterity-therapeutics-launches-ath434-phase-2-clinical-trial-for-the-treatment-of-patients-with-multiple-system-atrophy-301559919.html. Jun. 2, 2022.
Announcement. Alterity Launches ATH434 Phase 2 Clinical Trial. Jun. 2, 2022. https://alteritytx.com/announcements/4158677.
Announcement: First Patient dosed in ATH434 Phase 2 Clinical Trial. Jul. 6, 2022. https://alteritytx.com/announcements/4171281.
Announcement: Alterity Therapeutics Doses First Patient in ATH434 Phase 2 Clinical Trial in Multiple System Atrophy. https://alteritytx.com/announcements/4171281. Jul. 6, 2022.
Announcement: US FDA Approval for IND Application for ATH434 for MSA. Sep. 20, 2022. https://alteritytx.com/announcements/4203631.
Announcement: ATH434 Prevents Brain Cell loss in Parkinsons Animal Model. Jan. 30, 2023. https://alteritytx.com/announcements/4243657.
Announcement: First Patient Enrolled in Europe in Phase II Clinical trial. https://alteritytx.com/announcements/4332987. Mar. 8, 2023.
Announcement: First Patient Enrolled in USA in Phase II Clinical Trial. https://alteritytx.com/announcements/4336559. Mar. 16, 2023.
Announcement: First Patient Enrolled in UK in Phase II Clinical Trial. https://alteritytx.com/announcements/4343792. Apr. 4, 2023.
Announcement: First Patient Enrolled in Australia in global Phase 2 Trial. https://alteritytx.com/announcements/4357850. May 10, 2023.
Announcement: New Data Demonstrating Novel Mechanisms of ATH434. Nov. 16, 2023. https://alteritytx.com/announcements/5429434.
Announcement: Alterity Therapeutics Reports Positive Efficacy Data for ATH434 in a Primate Model of Parkinson's Disease. https://www.nasdaq.com/press-release/alterity-therapeutics-reports-positive-efficacy-data-for-ath434-in-a-primate-model-of. Dec. 4, 2023.
Announcement. Alterity Presents Data Describing Neuroprotection of ATH434. Oct. 11, 2024. https://alteritytx.com/announcements/6573278.
Announcement. Alterity Announces Publication on ATH434 Mechanism of Action. Nov. 6, 2024. https://alteritytx.com/announcements/6616294.
Announcement: Alterity Therapeutics Announces New Publication Describing Novel Mechanism of Action for ATH434. Nov. 6, 2024.
Announcement. New publication shows ATH434 rescues neurons in MSA model. Jan. 28, 2022. https://alteritytx.com/announcements/4081329.
Announcement. Positive ATH434 Phase 2 Results Led by Clinical Efficacy. Jan. 30, 2025. https://alteritytx.com/announcements/6770129.
Article: Multiple System Atrophy Agent ATH434 Shows Promising Topline Efficacy in Phase 2 Trial. https://www.neurologylive.com/view/multiple-system-atrophy-agent-ath434-shows-promising-topline-efficacy-phase-2-trial. Jan. 30, 2025.
Ausbiz interview with David Stamler. https://ausbiz.com.au/media/alterity-therapeutics-david-stamler?videoId=39141. Dec. 4, 2024.
Ausbiz interview with David Stamler. https://ausbiz.com.au/media/partner-content?videoId=39160. Dec. 8, 2024.
Bailey et al, Potent Antioxidant and Mitochondrial-protectant Effects of ATH434, 2023 https://alteritytherapeutics.com/wp-content/uploads/DB-SfN-2023-poster-for-PR_v2.pdf.
Bailey et al. Potent Antioxidant and Mitochondrial-protectant Effects of ATH434, a Novel Inhibitor of $\alpha$-Synuclein Aggregation with Moderate Iron-binding Affinity, 2024 https://alteritytherapeutics.com/wp-content/uploads/DB-sfn-2024-poster-10Oct24.pdf.
Beauchamp et al. ATH434 Rescues Pre-motor Hyposmia in a Mouse Model of Parkinsonism, 2022 https://link.springer.com/article/10.1007/s13311-022-01300-0.
Bond S. et al. ATH434, an iron chaperone for neurodegenerative diseases, AusIron 2024, Brisbane.
Bradbury et al. Effects of ATH434, a Clinical-Phase Small Molecule with Moderate Affinity for Iron, in Hemiparkinsonian Macaques, 2023 https://alteritytherapeutics.com/wp-content/uploads/Effects-of-ATH434_Dec01-2023.pdf.
Bradbury et al. Effects of ATH434, a Clinical-Phase Small Molecule with Moderate Affinity for Iron, in Hemiparkinsonian Macaques, 2024 https://alteritytherapeutics.com/wp-content/uploads/poster-MDS-2024-Bradbury-MPTP.pdf.
Bradbury et al. Effects of ATH434, a Clinical-phase Small Molecule with Moderate Affinity for Iron, in a Parkinson's Disease Model in Macaques [sic], 2024 https://alteritytherapeutics.com/wp-content/uploads/poster-Bradbury-AAN-2024-MPTP.pdf.
Claassen et al. Preliminary Efficacy and Safety of ATH434 in Multiple System Atrophy, 2024 https://alteritytherapeutics.com/wp-content/uploads/poster-MDS-2024-Claassen-202.pdf.
Clinical trial notification. A Phase 1 clinical trial to assess the safety, tolerability and pharmacokinetics of PBT434 in healthy volunteers. Jan. 18, 2019. https://www.anzctr.org.au/Trial/Registration/TrialReview.aspx?id=374741&isReview=true.
Clinical trial notification. A Phase 1 Study to Evaluate a Tablet Formulation of PBT434 in Healthy Volunteers. Nov. 20, 2020. https://www.anzctr.org.au/Trial/Registration/TrialReview.aspx?id=380631&isReview=true.
Clinical trial notification. Study of ATH434 in Participants with Multiple System Atrophy. Nov. 5, 2021. https://www.anzctr.org.au/Trial/Registration/TrialReview.aspx?id=20539&isClinicalTrial=True.
Clinical trial notification. Study of ATH434 in Participants with Multiple System Atrophy. Nov. 9, 2023. https://clinicaltrials.gov/study/NCT05109091.
Clinical trial notification. A Biomarker Study of ATH434 in Participants With MSA. Apr. 1, 2025. https://clinicaltrials.gov/study/NCT05864365.
Clinical trial notification. Study of ATH434 in Participants with Multiple System Atrophy https://ctv.veeva.com/study/study-of-ath434-in-participants-with-multiple-system-atrophy.
Clinical trial notification. Study of ATH434 in Participants With Multiple System Atrophy https://www.hra.nhs.uk/planning-and-improving-research/application-summaries/research-summaries/study-of-ath434-in-participants-with-multiple-system-atrophy/.
Daniel Claassen. Presentation: ATH434-201 Phase 2 Topline Results. Jan. 30, 2025. https://alteritytx.com/announcements/6770416.
Diwakarla S, et al. ATH434 Reverses Colorectal Dysfunction in the A53T Mouse Model of Parkinson's Disease. Journal of Parkinson's Disease. 2021;11(4):1821-1832. doi:10.3233/JPD-212731.
EU Clinical Trials Register. https://www.clinicaltrialsregister.eu/ctr-search/search?query=ATH434.
Finkelstein et al., The novel compound PBT434 prevents iron mediated neurodegeneration and alpha-synuclein toxicity in multiple models of Parkinson's disease, Acta Neuropathologica Communications, 2017, 53. https://actaneurocomms.biomedcentral.com/articles/10.1186/s40478-017-0456-2.
Finkelstein et al., PBT434 prevents the accumulation of glial cell inclusions and insoluble alpha-synuclein in a mouse model of Multiple System Atrophy. Mov Disord. 2018; 33 (suppl 2). https://www.mdsabstracts.org/abstract/pbt434-prevents-the-accumulation-of-glial-cell-inclusions-and-insoluble-alpha-synuclein-in-a-mouse-model-of-multiple-system-atrophy/.
Finkelstein et al. The Compound ATH434 Prevents Alpha-Synuclein Toxicity in a Murine Model of Multiple System Atrophy. Journal of Parkinson's Disease. 2022;12(1):105-115. doi:10.3233/JPD-212877.
Heras-Garvin et al., ATH434 Preserves Dopaminergic Neurons, Reduces $\alpha$-synuclein Oligomerization, and Improves Motor Function in a Transgenic Murine Multiple System Atrophy Model (1842), 2021, 96 (15 supplement.1842).

(56) References Cited

OTHER PUBLICATIONS

Heras-Garvin et al, ATH434 Reduces α-Synuclein-Related Neurodegeneration in a Murine Model of Multiple System Atrophy, Movement Disorders, 36 (11), p. 2605-2614.
https://alteritytherapeutics.com/pipeline/.
https://alteritytherapeutics.com/the-science/.
International Search Report and Written Opinion for WO 2026/011223 A1 (Alterity Therapeutics Limited).
Larvol Delta overview of AAN 2025 presentation. https://delta.larvol.com/Products/?ProductId=6238face-6014-45c6-871d-7e5255ff1946.
Lemos et al., Current experimental disease-modifying therapeutics for multiple system atrophy, Journal of Neural Transmission (2021) 128:1529-1543. https://doi.org/10.1007/s00702-021-02406-z.
Manufacturing services agreement for PBT434 supply https://www.sec.gov/Archives/edgar/data/1131343/000117891314003317/exhibit_4-36.htm.
MSA Agent ATH434 Shows Promising Phase 2 Data. https://www.neurologylive.com/view/msa-agent-ath434-promising-phase-2-data-fda-approves-suzetrigine-severe-acute-pain-axs-07-gains-fda-approval-migraine.
Pall et al. ATH434, a promising iron-targeting compound for treating iron regulation disorders, Metallomics. Oct. 4, 2024;16(10):mfae044 https://pubmed.ncbi.nlm.nih.gov/39317669/.
Pall et al. Biophysical Characteristics of ATH434, a Unique Iron-Targeting Drug for Treating Friedreich's Ataxia, 2024 https://alteritytherapeutics.com/wp-content/uploads/Biophysical-Characteristics-of-ATH434_Unique-iron-targeting-drug-for-treating-Friedreichs-Ataxia.pdf.
Press Release. Alterity Therapeutics Announces New Publication Describing Novel Mechanism of Action for ATH434. https://www.biospace.com/press-releases/alterity-therapeutics-announces-new-publication-describing-novel-mechanism-of-action-for-ath434. Nov. 6, 2024.
Stamler et al, A First in Human Study of PBT434, a Novel Small Molecule Inhibitor of α-Synuclein Aggregation (S4.001), 2019, https://n.neurology.org/content/92/15_Supplement/S4.001.
Stamler et al. A First in Human Study of PBT434, a Novel Small Molecule Inhibitor of Alpha-Synuclein Aggregation [abstract]. Mov Disord. 2019; 34 (suppl 2). https://www.mdsabstracts.org/abstract/a-first-in-human-study-of-pbt434-a-novel-small-molecule-inhibitor-of-alpha-synuclein-aggregation/.
Stamler et al, A Phase 1 Study of PBT434, a Novel Small Molecule Inhibitor of α-Synuclein Aggregation, in Adult and Older Adult Volunteers (4871), 2020, https://www.neurology.org/doi/10.1212/WNL.94.15_supplement.4871.
Stamler et al, Cardiovascular safety and pharmacokinetics of ATH434, a novel small molecule inhibitor of α-synuclein aggregation, in adults and older adults 2021. https://alteritytherapeutics.com/investor-centre/news/2021/11/09/alterity-therapeutics-announces-presentation-of-ath434-at-the-american-autonomic-society-virtual-meeting-2021/.
Stamler et al. A Phase 2 study of ATH434, a Novel Inhibitor of α-synuclein Aggregation, for the Treatment of Multiple System Atrophy, 2024 https://alteritytherapeutics.com/wp-content/uploads/poster-Stamler-AAN-2024-P2-Baseline.pdf.
Stamler et al. A Phase 2 study of ATH434, a Novel Inhibitor of α-synuclein Aggregation, for the Treatment of Multiple System Atrophy, 2024 https://alteritytherapeutics.com/wp-content/uploads/poster-MDS-2024-Stamler-201.pdf.
Stamler et al. ATH434 Slowed Disease Progression in a Phase 2 Study in Multiple System Atrophy https://alteritytherapeutics.com/wp-content/uploads/the-science/msa-2025-poster-stamler-201tld.pdf.
Stamler et al. A Randomized, Double Blind, Placebo Controlled Phase 2 Study of ATH434 in MSA, 2025 https://alteritytherapeutics.com/wp-content/uploads/a-randomized-double-blind-placebo-controlled-phase-2-study-of-ath434-in-msa-1.pdf.
Stamler et al. Topline data from a Randomized, Double Blind, Placebo Controlled Phase 2 Study of ATH434 in MSA, 2025 https://alteritytherapeutics.com/wp-content/uploads/the-science/aan-2025_ath434-201_oral-presentation.pdf.
Stamler et al. A Phase 2 Study of ATH434, a Novel Inhibitor of α-synuclein Aggregation, for the Treatment of Multiple System Atrophy (MSA) (P2-3.004) https://www.neurology.org/doi/10.1212/WNL.0000000000206596.
Stamler et al. Topline Data from a Randomized, Double Blind, Placebo Controlled Phase 2 Study of ATH434 in Multiple System Atrophy (S37.008) https://www.neurology.org/doi/10.1212/WNL.0000000000212526.
Stamler et al. Topline Data from a Randomized, Double Blind, Placebo Controlled Phase 2 Study of ATH434 in Multiple System Atrophy https://www.aan.com/msa/Public/Events/AbstractDetails/58512.
Stamler et al. A Phase 1 Study of PBT434, a Novel Small Molecule Inhibitor of α-Synuclein Aggregation, in Adult and Older Adult Volunteers (4871) https://www.neurology.org/doi/10.1212/WNL.94.15_supplement.4871#:~:text=Results%3A, 102.5%20to%20229.5%20ng%.
Stamler et al. A First in Human Study of PBT434, a Novel Small Molecule Inhibitor of α-Synuclein Aggregation (S4.001) https://www.neurology.org/doi/10.1212/WNL.92.15_supplement.S4.001.
YouTube: Alterity Therapeutics' phase 2 clinical trial nears, commercialisation plans continue for MSA drug. https://www.youtube.com/watch?v=m5-TI01dlsw. Mar. 12, 2021.
YouTube: Alterity Therapeutics at the International Congress of Parkinson's Disease and Movement Disorder. https://www.youtube.com/watch?v=4YRqWDauRb4. Oct. 2, 2024.
YouTube: Therapeutic potential of ATH434 in Multiple System Atrophy. https://www.youtube.com/watch?v=1BC92RXYZfQ. Oct. 19, 2024.
YouTube: Alterity Therapeutics' vision for neurodegenerative care. https://www.youtube.com/watch?v=73bVe7AuWrA. Dec. 6, 2024.
YouTube: Alterity Therapeutics Shareholder Webinar—ATH434-201 Phase 2 clinical study results. https://www.youtube.com/watch?v=6mbB9ipm2fo. Jan. 30, 2025.
International Application No. PCT/AU2026/050224, International Search Report mailed Apr. 30, 2026, 5 pages.
International Application No. PCT/AU2026/050224, Written Opinion of the International Searching Authority mailed Apr. 30, 2026, 8 pages.
International Application No. PCT/AU2026/050224, Search Information Statement (SIDS) completion date Apr. 30, 2026, 2 pages.

| ADC1232-63 | |
|---|---|
| RRT | AREA % |
| 0.84 | 0.01 |
| 0.88 | 0.06 |
| 0.96 | 0.01 |
| **1.00** | **99.89** |
| 1.04 | 0.01 |
| 1.14 | 0.02 |

CRYSTALLINE FORM, AND PROCESS FOR ITS PRODUCTION

RELATED APPLICATION

The present application claims the benefit of and priority to Australian Provisional Patent Application No. 2025900806 filed on 14 Mar. 2025, the entire contents of which are incorporated herein by this cross-reference.

FIELD

The present disclosure relates to a crystalline form (Form A) of a salt of a compound of formula (I) as defined herein. The present disclosure also relates to processes for the production of Form A of the salt, and to pharmaceutical compositions and therapeutic methods involving the salt and crystalline Form A.

BACKGROUND

According to the WHO, neurodegenerative conditions affect up to 1 billion people. Examples of such conditions include multiple system atrophy (MSA) and Parkinson's disease.

Multiple System Atrophy (MSA) is a rare, neurodegenerative disease characterized by failure of the autonomic nervous system and impaired movement. The symptoms reflect the progressive loss of function and death of different types of nerve cells in the brain and spinal cord. It is a rapidly progressive disease and causes profound disability. MSA is a Parkinsonian disorder characterized by a variable combination of slowed movement and/or rigidity, autonomic instability that affects involuntary functions such as blood pressure maintenance and bladder control, and impaired balance and/or coordination that predisposes to falls. A pathological hallmark of MSA is the accumulation of the protein α-synuclein within glia, the support cells of the central nervous system, and neuron loss in multiple brain regions. MSA affects approximately 15,000 individuals in the U.S., and while some of the symptoms of MSA can be treated with medications, currently there are no drugs that are able to slow disease progression and there is no cure.

Parkinson's disease (PD) is the second most common neurodegenerative disorder and causes unintended or uncontrollable movements of the body along with neuropsychiatric and other nonmotor features. The precise cause of PD is unknown, but some cases are hereditary while others are thought to occur from a combination of genetics and environmental factors that trigger the disease. In PD, brain cells become damaged or die in the substantia nigra, the part of the brain that produces dopamine—a chemical needed to produce smooth, purposeful movement. The cardinal symptoms of PD are tremors, rigidity, slowing of movements, and later in disease, impaired balance. Other symptoms may include difficulty swallowing, chewing, or speaking; emotional changes; urinary problems or constipation; dementia or other cognitive problems; fatigue; and problems sleeping. Nearly one million people in the U.S. and more than 10 million people worldwide are living with PD. Approximately 60,000 Americans are diagnosed with PD each year.

There is a strong unmet clinical need in relation to such neurodegenerative conditions, and a need to find agents that are capable of treating, preventing or reducing the symptoms of neurodegenerative conditions, such as MSA and PD.

The compound ATH434 has been proposed as a potential therapy for treatment of neurodegenerative conditions such as MSA and PD. ATH434 is an oral agent designed to inhibit the aggregation of pathological proteins implicated in neurodegeneration. ATH434 has been shown to reduce α-synuclein pathology and preserve neuronal function by restoring iron balance in the brain.

ATH434 has the structure:

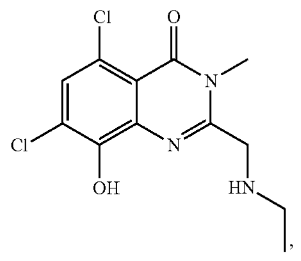 [SMILES: CCNCc1nc2c(O)c(Cl)cc(Cl)c2c(=O)n1C]

and is described in, for example, WO2005/095360 and U.S. Pat. No. 8,889,695.

Research and development to identify new therapies for the treatment of medical conditions such as neurodegenerative disorders, is a highly challenging task. It typically takes 10 years or longer for a new medicine to complete the journey from discovery to authorisation for use in the marketplace with there being a high rate of failure. Alongside being efficacious and safe to use, there are many other requirements for new medicinal products. For example, the active substance must be available in high levels of purity, with good reproducibility and being capable of being produced on large scale. The substance must also be physically and chemically stable over time, including on exposure to different temperature and humidity conditions.

Many organic compounds exist in a variety of solid forms, including as the free acid or base, or in salt form. Compounds or salts can also potentially exist as amorphous material and in crystalline form, and for some molecules a large number of different crystalline forms (polymorphs) may exist. Polymorphs of a given compound or salt can have different properties to each other, for example in respect of characteristics such as hygroscopicity, stability and solubility. Where a particular form of a compound is unstable or metastable, this can lead to difficulties during manufacture, storage and/or use of the compound.

Identification of solid forms of a pharmaceutical active agent, and in particular the discovery of a sold form having the required properties, is in many cases a challenging and unpredictable task, with it being unknown how many polymorphs there may be, what their respective characteristics will be, or what synthetic process might provide access to a polymorph.

It would be desirable to provide a solid form of the compound ATH434 having properties such as high stability and low hygroscopicity, and which can be produced in high purity in a reproducible and scalable manner.

It would also be desirable to provide processes enabling provision of such a solid form of ATH434 reproducibly and in high purity.

SUMMARY

The present disclosure is based at least in part on the discovery of a polymorphic form of ATH434 methanesulfonate salt (Form A), having desirable properties for use in a pharmaceutical product, such as stability and lack of hygroscopicity. Furthermore, processes enabling production of ATH434 methanesulfonate salt Form A which enable the Form A material to be produced reproducibly in high purity and good yield.

In a first aspect, there is provided a crystalline form (Form A) of the methanesulfonate salt of the compound of formula (I):

(I)

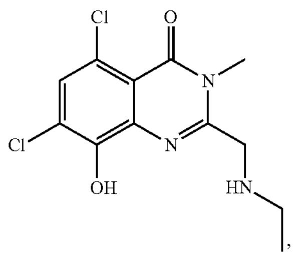

wherein the crystalline form exhibits an X-ray powder diffraction pattern comprising peaks at each of 16.5, 22.4, 22.7, 23.3 and 24.1 degrees 2θ±0.2 2θ as measured by X-ray powder diffraction.

In some embodiments, the crystalline form exhibits an X-ray powder diffraction pattern also comprising peaks at one or more of 8.4, 10.5, 14.6, 15.1, 15.5, 16.8, 17.3 and 21.4 degrees 2θ±0.2 2θ as measured by X-ray powder diffraction.

In some embodiments, the crystalline form exhibits an X-ray powder diffraction pattern also comprising peaks at each of 8.4, 10.5, 14.6, 15.1, 15.5, 16.5, 16.8, 17.3, 21.4, 22.4, 22.7, 23.3 and 24.1 degrees 2θ+0.2 2θ as measured by X-ray powder diffraction.

In some embodiments, the crystalline form exhibits an X-ray powder diffraction pattern substantially as shown in FIG. 4.

In some embodiments, the crystalline form has a differential scanning calorimetry profile showing an endothermic peak with peak onset at 291° C.±5° C. and peak at 292° C.±5° C.

In some embodiments, the crystalline form has a differential scanning calorimetry profile showing an endothermic peak with peak onset at 291° C.±2° C.

In some embodiments, the crystalline form exhibits loss of not more than 0.3% mass during heating to 250° C. when subjected to thermogravimetric analysis.

In some embodiments, the crystalline form is substantially unsolvated.

In some embodiments, the methanesulfonate salt of the compound of formula (I) has a purity of at least 98% by mass.

In another aspect, there is provided a pharmaceutical composition comprising: crystalline Form A as defined herein; and a pharmaceutically acceptable excipient and/or carrier.

In some embodiments, at least 90% by mass of the methanesulfonate salt of the compound of formula (I) in the pharmaceutical composition is in the crystalline form.

In some embodiments, at least 98% by mass of the methanesulfonate salt of the compound of formula (I) in the pharmaceutical composition is in the crystalline form.

In some embodiments, the methanesulfonate salt of the compound of formula (I) has a purity of at least 98% by mass.

In another aspect, there is provided a method of treating, preventing and/or reducing one or more symptoms of a neurological condition in a subject, comprising administering a therapeutically effective amount of crystalline Form A as defined herein, or of a pharmaceutical composition as defined herein, to the subject.

In another aspect, there is provided use of crystalline Form A as defined herein in the manufacture of a medicament for the treatment, prevention and/or reduction of one or more symptoms of a neurological condition.

In another aspect, there is provided crystalline Form A as defined herein, or a pharmaceutical composition as defined herein, for use in treating, preventing and/or reducing one or more symptoms of a neurological condition.

In some embodiments, the neurological condition is a neurodegenerative disease or disorder.

In some embodiments, the neurodegenerative disease or disorder is selected from the group consisting of Alzheimer's disease, amyotrophic lateral sclerosis, Parkinson's disease, Creutzfeldt-Jacob disease and its variant associated with "mad cow" disease, Huntington's disease, dementia with Lewvy body formation multiple system atrophy, Hallerboden-Spatz disease, diffuse Lewy body disease, fatal familial insomnia, Gertsmann Straussler Sheinker disease, hereditary cerebral haemorrhage with amyloidosis-Dutch type, multiple sclerosis, tauopathies, motor neuron disease and prion diseases.

In some embodiments, the neurodegenerative disease or disorder is selected from the group consisting of multiple system atrophy and Parkinson's disease.

In another aspect, there is provided a process for producing crystalline Form A as defined herein, comprising:

subjecting the methanesulfonate salt of the compound of formula (I):

(I)

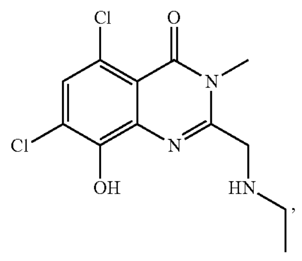

to crystallisation using an alcoholic solvent.

In some embodiments, the alcoholic solvent is a methanolic solvent.

In some embodiments, the alcoholic solvent is aqueous methanol in a methanol:water volume:volume ratio in the range of from 2:1 to 1:1.

In another aspect, there is provided a method of treating, preventing and/or reducing one or more symptoms of a neurological condition in a subject, comprising administering a therapeutically effective amount of a methanesulfonate salt of a compound of formula (I):

(I)

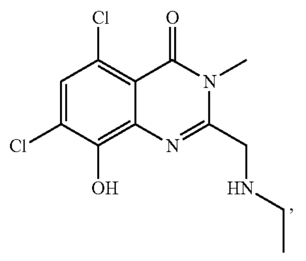

or of a pharmaceutical composition comprising a methanesulfonate salt of a compound of formula (I) and a pharmaceutically acceptable excipient and/or carrier, to the subject.

In another aspect, there is provided use of a methanesulfonate salt of a compound of formula (I):

(I)

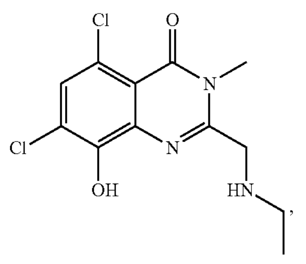

for the manufacture of a medicament for the treatment, prevention and/or reduction of one or more symptoms of a neurological disorder.

In another aspect, there is provided a methanesulfonate salt of a compound of formula (I):

(I)

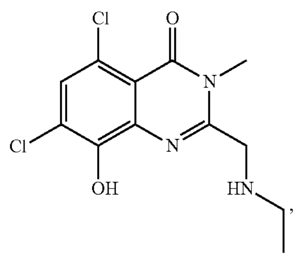

or a pharmaceutical composition comprising a methanesulfonate salt of a compound of formula (I) and a pharmaceutically acceptable carrier and/or excipient, for use in treating, preventing and/or reducing one or more symptoms of a neurological disorder.

In some embodiments, the neurological condition is a neurodegenerative disease or disorder.

In some embodiments, the neurodegenerative disease or disorder is selected from the group consisting of Alzheimer's disease, amryotrophic lateral sclerosis, Parkinson's disease, Creutzfeldt-Jacob disease and its variant associated with "mad cow" disease, Huntington's disease, dementia with Lewy body formation, multiple system atrophy, Hallerboden-Spatz disease, diffuse Lewy body disease, fatal familial insomnia, Gertsmann Straussler Sheinker disease, hereditary cerebral haemorrhage with amyloidosis-Dutch type, multiple sclerosis, tauopathies, motor neuron disease and prion diseases.

In some embodiments, the neurodegenerative disease or disorder is selected from the group consisting of multiple system atrophy and Parkinson's disease.

DETAILED DESCRIPTION

Definitions

Figure 1:
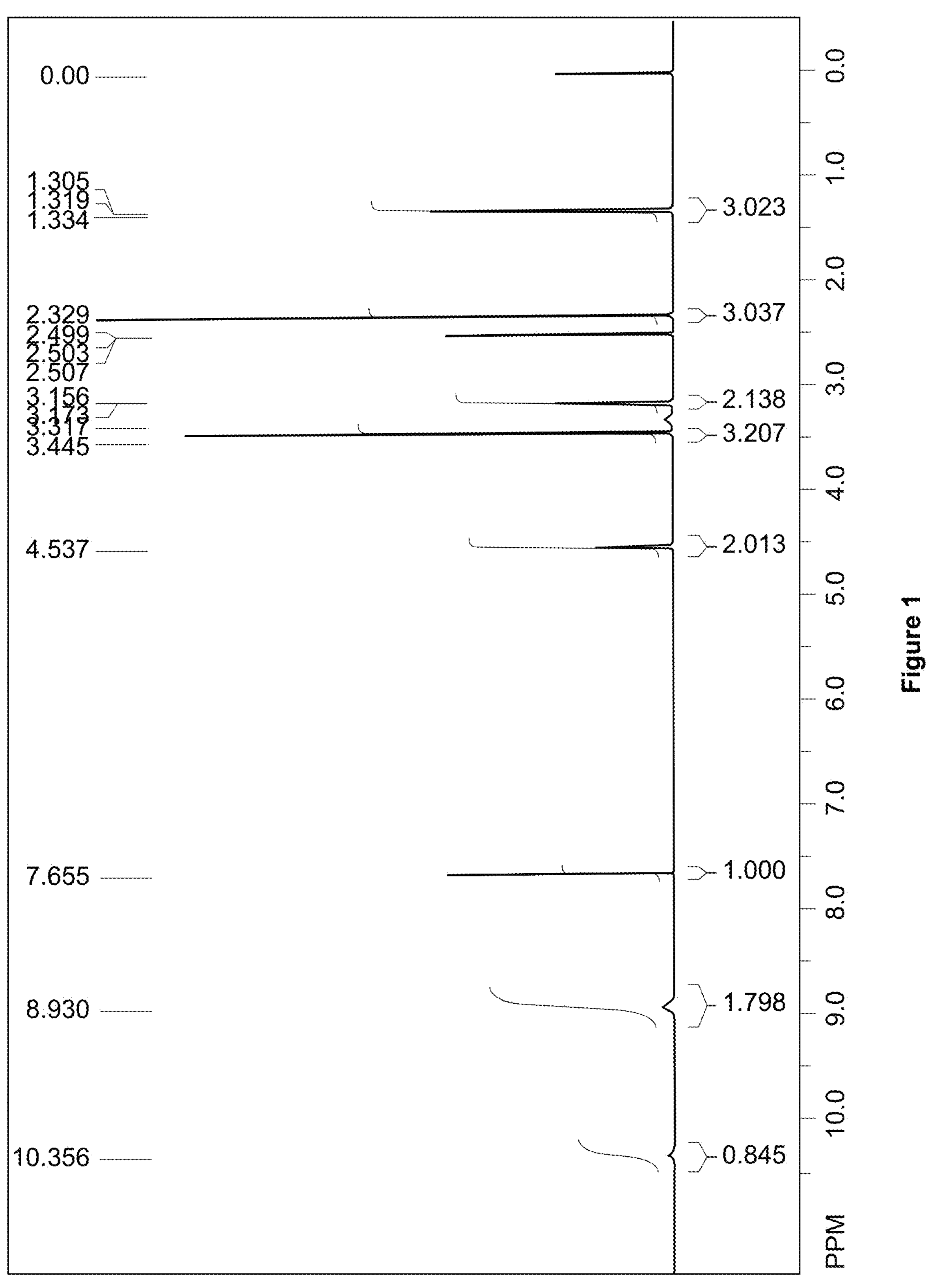
FIG. 1 shows a $^1$H NMR spectrum of a batch of ATH434 methanesulfonate salt Form A.

Unless specifically defined otherwise, all technical and scientific terms used herein shall be taken to have the same meaning as commonly understood by one of ordinary skill in the art.

Although any methods and materials similar or equivalent to those described herein can be used in the practice or testing of the present invention, preferred methods and materials are described. For the purposes of the present invention, the following terms are defined below.

The present disclosure may refer to the contents of certain documents being incorporated herein by reference. In the event of any inconsistent teaching between the teaching of the present disclosure and the contents of those documents, the teaching of the present disclosure takes precedence.

It is to be understood that if any prior art publication is referred to herein, such reference does not constitute an admission that the publication forms a part of the common general knowledge in the art.

As used herein, the term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10%, of the designated value.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Unless otherwise indicated, terms such as "first," "second," etc. are used herein merely as labels, and are not intended to impose ordinal, positional, or hierarchical requirements on the items to which these terms refer. More-over, reference to a "second" item does not require or preclude the existence of lower-numbered item (e.g., a "first" item) and/or a higher-numbered item (e.g., a "third" item).

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example and without limitation, two of item A, one of item B, and ten of item C; four of item B and seven of item C; or some other suitable combination.

As used herein, the word "comprise" and other forms of the word, such as "comprising" and "comprises," means including but not limited to, and is not intended to exclude, for example, other additives, components, integers, or steps.

As used herein, the term "subject" means an organism that is susceptible to a disease or condition. For example, the subject can be an animal, a mammal, a primate, a livestock animal (e.g., sheep, cow, horse, pig), a companion animal (e.g., dog, cat), or a laboratory animal (e.g., mouse, rabbit, rat, guinea pig, hamster). In some embodiments, the subject is a mammal. In some embodiments, the subject is human.

As used herein, the term "treating" includes curing a disease or disorder, as well as alleviation of or reduction of symptoms associated with a disease or disorder or condition. The term treating also includes slowing the progression of a disease or disorder.

As used herein, the term "prevention" includes prophylaxis, and includes reducing the likelihood of contracting a disease or disorder or a symptom thereof.

Each embodiment of the present disclosure described herein is to be applied mutatis mutandis to each and every other embodiment unless specifically stated otherwise or required otherwise by context.

Compound of Formula (I), Salt and Crystalline Form

The present disclosure relates to crystalline forms of the compound of formula (I):

(I)

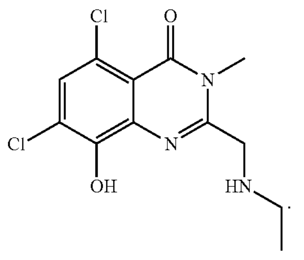

More particularly the present disclosure relates to crystalline forms of the methanesulfonate salt of the compound of formula (I).

The compound of formula (I) is referred to as ATH434, and has also been known as PBT-434. It has the molecular formula $C_{12}H_{13}Cl_2N_3O_2$.

The compound of formula (I), its preparation, and/or use in therapeutic applications, are disclosed in, for example WO2005/095360 and U.S. Pat. No. 8,889,695, the entire contents of each of which are incorporated herein by reference.

More particularly the present disclosure relates to the methanesulfonate salt of the compound of formula (I), and crystalline forms of the methanesulfonate salt of the compound of formula (I):

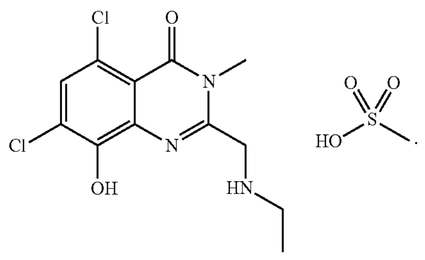

The salt has the molecular formula $C_{13}H_{17}Cl_2N_3O_5S$. A methanesulfonate salt can also be referred to as a mesylate salt.

In one aspect, there is provided a crystalline form (Form A) of the methanesulfonate salt of the compound of formula (I):

(I)

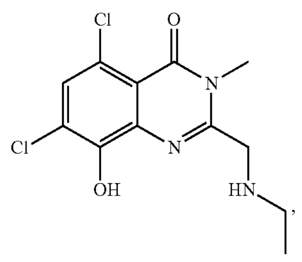

wherein the crystalline form exhibits an X-ray powder diffraction pattern comprising peaks at each of 16.5, 22.4, 22.7, 23.3 and 24.1 degrees 2θ±0.2 2θ as measured by X-ray powder diffraction.

Crystalline Form A of the methane sulfonate salt of the compound of formula (I) is producible as a highly crystalline material. The crystalline form is typically not a solvate, has good stability, and has low hygroscopicity. The crystalline form also has solubility characteristics suitable for use as a pharmaceutical active agent. The crystalline form can also be produced in good yield and with high purity.

Characterisation of the crystalline form by X-ray powder diffraction indicates the presence of distinctive peaks at 16.5, 22.4, 22.7, 23.3 and 24.1 degrees 2θ+0.2 2θ, obtained using the copper wavelengths $\lambda_1$ and $\lambda_2$ of 1.54056 Å and 1.54439 Å.

In some embodiments, the crystalline form exhibits an X-ray powder diffraction pattern comprising peaks at each of 16.5, 22.4, 22.7, 23.3 and 24.1 degrees 2θ 0.1 20 as measured by X-ray powder diffraction.

In some embodiments, the crystalline form exhibits an X-ray powder diffraction pattern comprising peaks at each of 16.5, 22.4, 22.7, 23.3 and 24.1 degrees 2θ±0.2 2θ as measured by X-ray powder diffraction, obtained using the copper wavelengths $\lambda_1$ and $\lambda_2$ of 1.54056 Å and 1.54439 Å.

In some embodiments, the crystalline form exhibits an X-ray powder diffraction pattern comprising peaks at each of 16.5, 22.4, 22.7, 23.3 and 24.1 degrees 2θ 0.1 20 as measured by X-ray powder diffraction, obtained using the copper wavelengths $\lambda_1$ and $\lambda_2$ of 1.54056 Å and 1.54439 Å.

Characterisation of the Form A crystalline form by X-ray powder diffraction also indicates the presence of further distinctive peaks at 8.4, 10.5, 14.6, 15.1, 15.5, 16.8, 17.3 and 21.4 degrees 2θ±0.2 2θ, obtained using the copper wavelengths $\lambda_1$ and $\lambda_2$ of 1.54056 Å and 1.54439 Å.

Thus, in some embodiments, the crystalline form exhibits an X-ray powder diffraction pattern comprising one or more peaks at any of 8.4, 10.5, 14.6, 15.1, 15.5, 16.8, 17.3 and 21.4 degrees 2θ±0.3 20 (e.g. obtained using the copper wavelengths $\lambda_1$ and $\lambda_2$ of 1.54056 Å and 1.54439 Å).

In some embodiments, the crystalline form exhibits an X-ray powder diffraction pattern comprising one or more peaks at any of 8.4, 10.5, 14.6, 15.1, 15.5, 16.8, 17.3 and 21.4 degrees 2θ±0.1 20 (e.g. obtained using the copper wavelengths $\lambda_1$ and $\lambda_2$ of 1.54056 Å and 1.54439 Å).

In some embodiments, the crystalline form exhibits an X-ray powder diffraction pattern comprising peaks at each of 8.4, 10.5, 14.6, 15.1, 15.5, 16.5, 16.8, 17.3, 21.4, 22.4, 22.7, 23.3 and 24.1 degrees 2θ±0.2 2θ (e.g. obtained using the copper wavelengths $\lambda_1$ and $\lambda_2$ of 1.54056 Å and 1.54439 Å).

In some embodiments, the crystalline form exhibits an X-ray powder diffraction pattern comprising peaks at each of 8.4, 10.5, 14.6, 15.1, 15.5, 16.5, 16.8, 17.3, 21.4, 22.4, 22.7, 23.3 and 24.1 degrees 2θ±0.1 20 (e.g. obtained using the copper wavelengths $\lambda_1$ and $\lambda_2$ of 1.54056 Å and 1.54439 Å).

In some embodiments, the crystalline form exhibits an X-ray powder diffraction pattern comprising peaks at 16.5, 22.4, 22.7, 23.3 and 24.1 degrees 2θ±0.2 2θ, and additionally comprises 1 or more, or 2 or more, or 3 or more, or 4 or more, or 5 or more, or 6 or more, or 7 or more, or 8, peaks selected from the group consisting of 8.4, 10.5, 14.6, 15.1, 15.5, 16.8, 17.3 and 21.4 degrees 2θ±0.1 20 (e.g. obtained using the copper wavelengths$_1$ and $\lambda_2$ of 1.54056 Å and 1.54439 Å).

In some embodiments, the crystalline form exhibits an X-ray powder diffraction pattern substantially comprising peaks at the degrees 2θ values (±0.2 2θ) indicated in the table below.

| Position (2θ) | d-value (Å) | Relative Intensity |
|---|---|---|
| 8.4 | 10.55 | 23 |
| 10.5 | 8.43 | 26 |
| 13.3 | 6.65 | 16 |
| 14.6 | 6.06 | 23 |
| 15.1 | 5.85 | 24 |
| 15.5 | 5.70 | 23 |
| 15.9 | 5.56 | 18 |
| 16.5 | 5.38 | 82 |
| 16.8 | 5.29 | 36 |
| 17.3 | 5.14 | 51 |
| 18.4 | 4.82 | 10 |
| 19.0 | 4.66 | 16 |
| 19.3 | 4.61 | 18 |
| 20.3 | 4.38 | 13 |
| 21.1 | 4.22 | 12 |
| 21.4 | 4.15 | 34 |
| 21.7 | 4.09 | 11 |
| 22.0 | 4.04 | 12 |
| 22.4 | 3.97 | 67 |
| 22.7 | 3.92 | 100 |
| 23.3 | 3.81 | 34 |
| 24.1 | 3.69 | 48 |
| 24.6 | 3.62 | 14 |
| 25.4 | 3.50 | 19 |

In some embodiments, the crystalline form exhibits an X-ray powder diffraction pattern substantially comprising peaks at the degrees 2θ values (±0.1 2θ) indicated in the table above.

Figure 4:
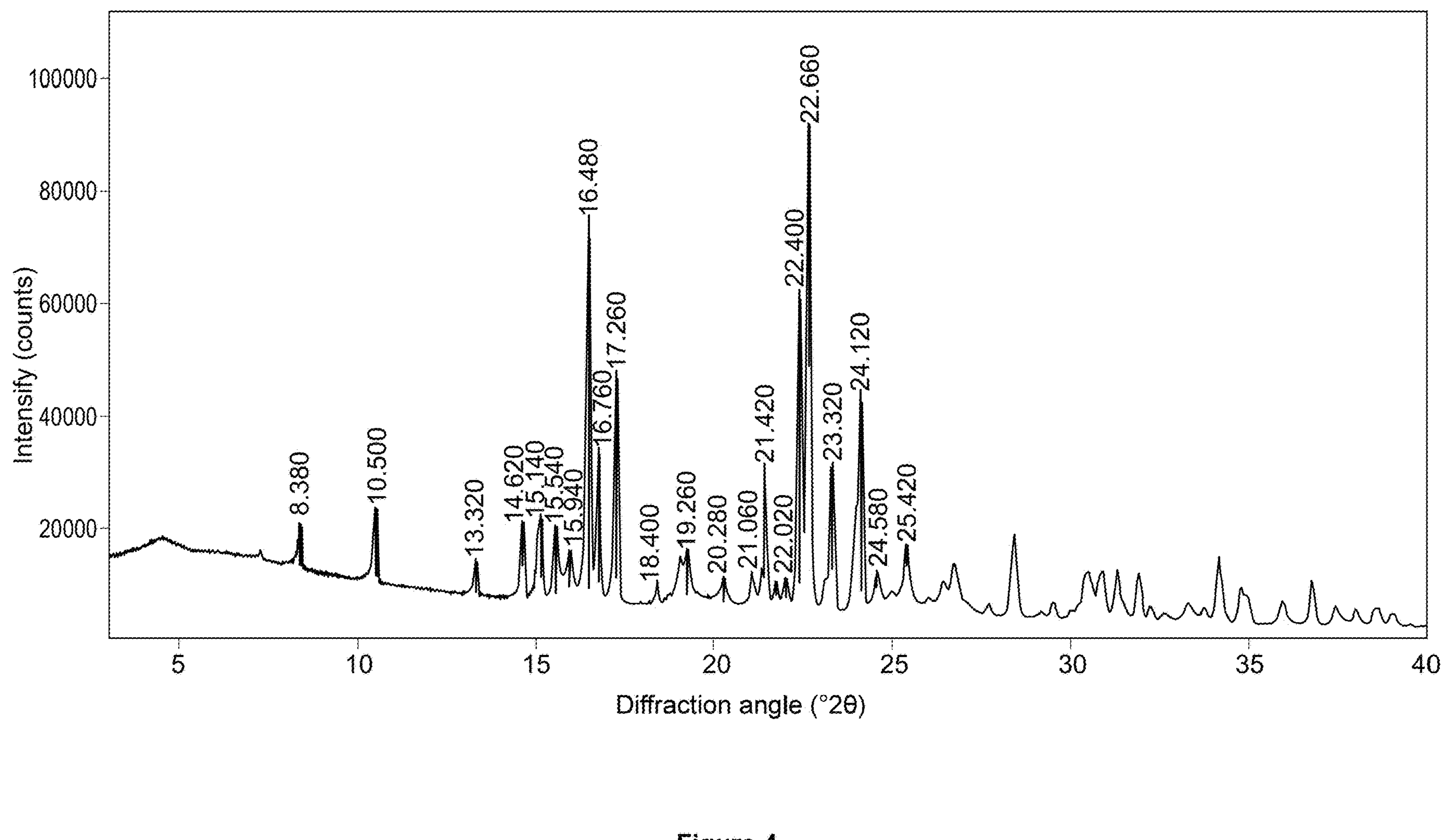
FIG. 4 shows an X-ray powder diffractogram of a batch of ATH434 methanesulfonate salt Form A.

In some embodiments, the crystalline form exhibits an X-ray powder diffraction pattern substantially as shown in FIG. 4.

Exemplary conditions for characterisation of the Form A crystalline form by X-ray powder diffraction include those set out at 2.9.33 of the European Pharmacopoeia 11.0, or at <941> of the US Pharmacopoeia.

Exemplary conditions for characterisation of the Form A crystalline form include use of a Bruker D8-Advance diffractometer, or a Bruker AXS C2 GADDS diffractometer, or for example using a PANalytical X'Pert Pro diffractometer. Conditions may for example be the following: Cu tube anode, 40 kV generator tension; 40 mA generator current; $\alpha_1$ wavelength of 1.54056 Å; $\alpha_2$ wavelength of 1.54439 Å; intensity ratio ($\alpha_2/\alpha_1$) of 0.5; spinner off, 200 angular range of 3.00-50.00; 200 step size of 0.02 2θ°; and/or time per step of 0.5 seconds.

Exemplary conditions for characterisation of the Form A crystalline form may alternatively or in addition include use of a Rigaku SmartLab X-Ray Diffractometer configured in Bragg-Brentano reflection or horizontal transmission geometry. A beam stop and knife edge to reduce incident beam and air scatter may be used in reflection mode. Exemplary data collection parameters are shown in the Table below.

| Parameter | Value | Parameter | Value |
|---|---|---|---|
| Geometry | Bragg-Brentano | Receiving Slit 1 (mm) | 18 |
| Tube Anode | Cu | Receiving Slit 2 (mm) | 20.1/Open |
| Tube Type | Long Fine Focus | Start Angle 2θ (°) | 2/3 |
| Tube Voltage (kV) | 40 | End Angle 2θ (°) | 40 |
| Tube Current (mA) | 44/50 | Step Size (°) | 0.02 |
| Detector | HyPix-3000/DteX250 | Scan Speed (°/min) | 6/2 |
| Monochromator | Ni foil Cu Kβ Filter/None | Spinning (rpm) | 11 |
| Incident Slit (°) | 1/3 | Sample Holder | Low-background Si/Transmission holder with Etnom films |

Characterisation of a typical batch of the Form A crystalline form by differential scanning calorimetry (DSC) has been shown to result in a DSC profile showing an endothermic peak with peak onset at about 291° C. and peak at 292° C.

Thus, in some embodiments, the crystalline form has a DSC profile showing an endothermic peak with peak onset at 291° C.±5° C. and peak at 292° C.±5° C.

In some embodiments, the crystalline form has a DSC profile showing an endothermic peak with peak onset at 291° C.±2° C. and peak at 292° C.±2° C.

In some embodiments, the crystalline form has a DSC profile showing an endothermic peak with peak onset at 291° C.±1° C. and peak at 292° C.±1° C.

Exemplary conditions for characterisation of the Form A crystalline form by DSC include those set out at 2.2.34 of the European Pharmacopoeia 11.0, or at <891> of the US Pharmacopoeia.

Exemplary conditions for characterisation of the Form A crystalline form by DSC include use of a TA Instruments Discovery DSC. For example, DSC analysis may be carried out by recording heat flow from 25 to 300° C. using a linear heating rate of 10° C./min.

Characterisation of a typical batch of the Form A crystalline form by thermogravimetric analysis (TGA) has been shown to result in low loss of mass during heating to 250° C.

In some embodiments, the crystalline form exhibits loss of not more than 1.0% mass during heating to 250° C. when subjected to thermogravimetric analysis.

In some embodiments, the crystalline form exhibits loss of not more than 0.5% mass during heating to 250° C. when subjected to thermogravimetric analysis.

In some embodiments, the crystalline form exhibits loss of not more than 0.3% mass during heating to 250° C. when subjected to thermogravimetric analysis.

Exemplary conditions for characterisation of the Form A crystalline form by TG include those set out at 2.2.34 of the European Pharmacopoeia 11.0, or at <891> of the US Pharmacopoeia.

Exemplary conditions for characterisation of the Form A crystalline form by TGA include use of a TA Instruments Discovery TGA. For example, TGA may be carried out by heating from ambient temperature to 350° C. using a linear heating rate of 10° C./min, under nitrogen flow (e.g. 25 mL/min), using 5-10 mg of sample for the measurement.

Many organic compounds can form complexes in solvents in which they are reacted or from which they are precipitated or crystallized. These complexes are known as "solvates". For example, a complex with water is known as a "hydrate". Solvates, such as hydrates, exist when the compound incorporates solvent.

In some embodiments, the crystalline form contains not more than 1.0% by weight of a solvent (e.g. an organic solvent and/or water). In some embodiments, the crystalline form contains not more than 0.5% by weight of a solvent (e.g. an organic solvent and/or water). In some embodiments, the crystalline form contains not more than 0.3% by weight of a solvent (e.g. an organic solvent and/or water). In some embodiments, the crystalline form contains not more than 0.2% by weight of a solvent (e.g. an organic solvent and/or water). In some embodiments, the crystalline form contains not more than 0.1% by weight of a solvent (e.g. an organic solvent and/or water).

In some embodiments, the crystalline form is unsolvated or substantially unsolvated (e.g. it is substantially free of solvated water or organic solvent).

In some embodiments, the crystalline Form A of the methanesulfonate salt of the compound of formula (I) has a purity of at least 97%, or at least 97.5%, or at least 98%, or at least 98.5%, or at least 99%, or at least 99.5% (e.g. when measured by HPLC and/or when measured by $^1$H NMR).

In some embodiments, disclosed herein is a composition of the methanesulfonate salt of the compound of formula (I). In some embodiments, the composition comprises the methanesulfonate salt of the compound of formula (I) in an amorphous form, in crystalline form A, or both. In some embodiments, at least 90% by mass of the methanesulfonate salt of the compound of formula (I) in the composition is in the crystalline form described herein (e.g., form A). In some embodiments, at least 95% by mass of the methanesulfonate salt of the compound of formula (I) in the composition is in the crystalline form described herein (e.g., form A). In some embodiments, at least 98% by mass of the methanesulfonate salt of the compound of formula (I) in the composition is in the crystalline form described herein (e.g., form A). In some embodiments, at least 99% by mass of the methanesulfonate salt of the compound of formula (I) in the composition is in the crystalline form described herein (e.g., form A).

In some embodiments, the crystalline Form A of the methanesulfonate salt of the compound of formula (I) is a crystalline form obtained or obtainable by crystallisation of the methanesulfonate salt of the compound of formula (I) using an alcoholic solvent.

In some embodiments, the crystalline Form A of the methanesulfonate salt of the compound of formula (I) is a crystalline form obtained or obtainable by crystallisation of the methanesulfonate salt of the compound of formula (I) using an aqueous methanol solvent.

Preparation of Crystalline Form A

In another aspect, there is provided a process for producing crystalline Form A as defined herein, comprising:

subjecting the methanesulfonate salt of the compound of formula (I):

(I)

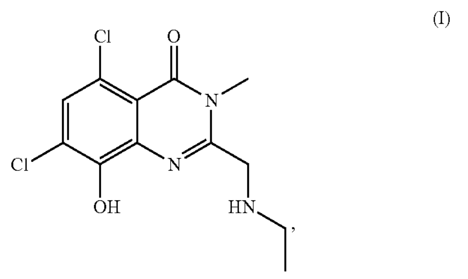 [SMILES: CCNCc1nc2c(O)c(Cl)cc(Cl)c2c(=O)n1C]

to crystallisation using an alcoholic solvent.

It has been found that the process can provide the Form A crystalline form reproducibly, in good yield, high purity, and in a scalable manner.

The formation of crystalline form A may for example be carried out under ambient atmosphere, or under an inert atmosphere such as nitrogen or argon.

Any suitable alcoholic solvent may be used for the crystallisation. In some embodiments, the solvent consists of an alcohol. In some embodiments, the solvent is a mixture of an alcohol and another solvent, such as water or a polar organic solvent such as acetonitrile or tetrahydrofuran. In some embodiments, the alcohol is methanol. In some embodiments, a mixture of methanol and acetonitrile is used. In some embodiments, a mixture of methanol and tetrahydrofuran is used. In some embodiments, a mixture of methanol and water is used, i.e. the alcoholic solvent is aqueous methanol.

Where a mixture of solvents is used, any suitable volume ratio of the solvents may be utilised. In some embodiments, where a mixture of methanol and water is used, the volume ratio of methanol to water is in the range of from 2:8 to 6:4. or from 3:7 to 5:5, or about 4:6. In some embodiments, where a mixture of methanol and water is used, the volume: volume ratio of methanol to water is in the range of from 2:1 to 1:1, or from 1.6:1 to 1.5:1, or about 1.5:1.

Any suitable volume of solvent may be utilised for the crystallisation. The amount used will depend on the amount of ATH434 methanesulfonate salt Form A to be produced. In some embodiments, the amount of solvent used for the crystallisation is in the range of from 10 to volumes (i.e. from 10 mL to 25 mL per g of ATH434 methanesulfonate salt). In some embodiments, the amount of solvent used for the crystallisation is in the range of from 12 to volumes, or from 13 to 19 volumes, or from 14 to 18 volumes, or from 15 to 17 volumes, or about 16 volumes.

In some embodiments, a mixture of methanol and water is used, in a volume ratio of from 3:7 to 5:5, or about 4:6, or from 2:1 to 1:1, or from 1.6:1 to 1.5:1, or about 1.5:1, and the amount of solvent used is in the range of from 12 to 20 volumes (i.e. from 12 mL to 20 mL per g of ATH434 methanesulfonate salt), or in the range of from 14 to 18 volumes, or about 16 volumes.

Any suitable temperature conditions may be used for the crystallisation. In some embodiments, a mixture containing ATH434 methanesulfonate salt and solvent is heated to a temperature at which the ATH434 methanesulfonate salt dissolves, is held at that temperature for a period of time, and the temperature is then allowed to decrease gradually.

In some embodiments, a mixture containing ATH434 methanesulfonate salt and methanol is heated to a temperature at which the ATH434 methanesulfonate salt dissolves (e.g. a temperature of at least 60° C., for example a temperature of 62.5±2.5° C.), is held at that temperature for a period of time (e.g. about 30 minutes), water then added, and the temperature is then allowed to decrease gradually, for example to a temperature of 43.5±0.3.5° C., with the mixture then being held at that temperature for a period of time (e.g. about 30 minutes). The mixture may for example then be cooled further, e.g. to 0-5° C. over a period of time (e.g. over 3 hours or more), and then be held at that temperature for a period (e.g. 2 hours or more).

The resulting solid may then be obtained by any suitable process, for example by filtration. The solid may be subjected to one or more washing, filtration and/or drying steps (e.g. under vacuum).

The crystallisation step may be repeated if desired.

ATH434 methanesulfonate salt may for example be produced from ATH434 free base, for example by dissolution of the free base in a suitable solvent such as methanol followed by addition of methanesulfonic acid, e.g. at ambient temperature. The methanesulfonate salt may be obtained by, for example, partial removal of the solvent by distillation (e.g. under vacuum) and filtration.

In some embodiments, ATH434 free base may be produced from another salt of ATH434, for example by treating the salt with a base such as sodium hydrogen carbonate in an appropriate solvent (e.g. water). The reaction may be carried out at any suitable temperature, for example at room temperature.

Purification of material and/or separation from impurities or byproducts may be carried out if desired, using any suitable technique, such as crystallisation, decanting, distillation, washing, dissolution in solvent and extraction/washing, and chromatography.

ATH434 may be produced by any suitable method, for example as described in WO2005/095360 or U.S. Pat. No. 8,889,695, or as set out in the examples section below.

Pharmaceutical Compositions

In some embodiments, crystalline form A of the methanesulfonate salt of the compound of formula (I) is provided in the form of a pharmaceutical composition, e.g. for use in treatment of a disease or disorder as defined herein.

Accordingly, there is also provided a pharmaceutical composition comprising crystalline Form A of the methanesulfonate salt of the compound of formula (I); and a pharmaceutically acceptable excipient and/or carrier.

In some embodiments, at least 90% by mass of the methanesulfonate salt of the compound of formula (I) in the pharmaceutical composition is in the crystalline form described herein (e.g., form A). In some embodiments, at least 95% by mass of the methanesulfonate salt of the compound of formula (I) in the pharmaceutical composition is in the crystalline form described herein (e.g., form A). In some embodiments, at least 98% by mass of the methanesulfonate salt of the compound of formula (I) in the pharmaceutical composition is in the crystalline form described herein (e.g., form A). In some embodiments, at least 99% by mass of the methanesulfonate salt of the compound of formula (I) in the pharmaceutical composition is in the crystalline form described herein (e.g., form A). The amount of a certain polymorphic form in a composition can be determined by methods known in the art, e.g., X-ray Powder Diffraction, near infrared spectrometry, a combination of techniques, etc.

In some embodiments, the methanesulfonate salt of the compound of formula (I) has a purity of at least 90% by mass in the pharmaceutical composition. In some embodiments, the methanesulfonate salt of the compound of formula (I) has a purity of at least 95% by mass in the pharmaceutical composition. In some embodiments, the methanesulfonate salt of the compound of formula (I) has a purity of at least 98% by mass in the pharmaceutical composition. In some embodiments, the methanesulfonate salt of the compound of formula (I) has a purity of at least 99% by mass in the pharmaceutical composition.

Suitably, the pharmaceutical composition comprises a pharmaceutically acceptable excipient and/or carrier. By "pharmaceutically acceptable excipient" is meant a solid or liquid filler, diluent or encapsulating substance, or any other pharmaceutically acceptable excipient, such as a binder, disintegrant, lubricant, anti-caking agent, coloring, preservative, antioxidant, buffer or pH-adjusting agent, that may be safely used.

The pharmaceutical compositions described herein may be provided in unit dosage form. As used herein, a "unit dosage form" means a composition in a form containing an amount of a compound or salt sufficient to provide a single dose or part-single dose of that compound or salt. Examples of unit dosage forms include pills, capsules, caplets, tablets, sachets, and the like.

The pharmaceutical composition may be formulated for delivery by any suitable route of administration, such as for example topical, rectal, parenteral, sublingual, buccal, intravenous, intraarticular, intra-muscular, intra-dermal, subcutaneous, inhalational, intraocular, intraperitoneal, intracerebroventricular, transdermal and the like.

Compositions can be prepared according to conventional methods, e.g. dissolution, suspension, mixing, granulating or coating methods.

Examples of dosage forms include tablets, capsules, caplets, dispersions, suspensions, injections, solutions, syrups, troches, capsules, suppositories, aerosols, transdermal patches, impregnated (occlusive) dressing, creams, gels and the like. These dosage forms may also include injecting or implanting devices designed specifically for, or modified to achieve, controlled release of the pharmaceutical composition.

Controlled release of the therapeutic agent may be affected, for example by coating the same with hydrophobic polymers including acrylic resins, waxes, higher aliphatic alcohols, polylactic and polyglycolic acids and certain cellulose derivates such as hydroxypropylmethyl cellulose. In addition, the controlled release may be affected by using other polymer matrices, liposomes and/or microspheres.

Depending upon the particular route of administration, a variety of carriers, well known in the art may be used. For example, these carriers or excipients may be selected from a group including sugars, starches, cellulose and its derivates, malt, gelatine or other gelling agents, talc, calcium sulphate, vegetable oils, synthetic oils, alcohols and/or polyols, alginic acid, phosphate buffered solutions, emulsifiers, isotonic saline, and pyrogen-free water.

Pharmaceutically acceptable carriers and acceptable carriers for systemic administration may for example be incorporated into the compositions of this disclosure.

Pharmaceutical compositions of the present disclosure suitable for administration may for example be presented in discrete units such as syringes, vials, tubes, capsules, sachets or tablets each containing a predetermined amount of crystalline Form A of the methanesulfonate salt of the compound of formula (I), as a powder or granules or as a solution or a suspension in an aqueous liquid, a cyclodextrin solution, a non-aqueous liquid, an oil-in-water emulsion or a water-in-oil emulsion or as a solution or suspension in a cream or gel or as a suspension of micro- or nano-particles, including but not limited to silica or polylactide micro- or nano-particles.

Such compositions may be prepared by any of the methods of pharmacy, but methods may for example include the step of bringing into association Form A of the methanesulfonate salt of the compound of formula (I) with the carrier which constitutes one or more necessary ingredients. In many cases, the compositions are prepared by uniformly and intimately admixing active agent with liquid carriers or finely divided solid carriers or both, and then, if necessary, shaping the product into the desired presentation.

In powders, the carrier may for example be a finely divided solid which is in a mixture with the finely divided active component.

In tablets, the active component may for example be mixed with the carrier having the necessary binding capacity in suitable proportions and compacted into the shape and size desired.

Suitable carriers for powders and tablets include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included.

Tablets, powders, capsules, pills, cachets, and lozenges can be used as solid forms suitable for oral administration.

For preparing suppositories, a low melting wax, such as admixture of fatty acid glycerides or cocoa butter, may for example first be melted and the active component then dispersed homogeneously therein, as by stirring. The molten homogenous mixture can then be poured into convenient sized moulds, allowed to cool, and thereby to solidify.

Formulations suitable for vaginal administration may for example be presented as pessaries, tampons, creams, gels, pastes, foams or sprays containing, in addition to the active ingredient, such carriers as are known in the art to be appropriate.

Liquid form preparations include solutions, suspensions, and emulsions, for example, water or water-propylene glycol solutions. For example, parenteral injection liquid preparations can be formulated as solutions in aqueous 1,2-propanediol, dimethylsulfoxide (DMSO), aqueous solutions of gamma cyclodextrin or 2-hydroxypropyl-beta-cyclodextrin, saline solution or polyethylene glycol solution, with or without buffer. A preferred range of pH is 3.5-4.5. Suitable buffers buffer the preparation at pH 3.5-4.5 and include, but are not limited to, acetate buffer and citrate buffer.

Crystalline Form A of the salt of the compound of formula (I) may for example be formulated for parenteral administration (e.g. by injection, for example bolus injection or continuous infusion) and may be presented in unit dose form in ampoules, pre-filled syringes, small volume infusion or in multi-dose containers with an added preservative. The compositions may for example take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by, for example, dissolving the active component in water and adding suitable colorants, flavours, stabilizing and/or thickening agents, as desired.

Aqueous suspensions suitable for oral use can be made by, for example, dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis or other organ, crystalline Form A may for example be formulated as a gel, ointment, emulsion, paste, cream or lotion, or as a transdermal patch. Gels may for example be prepared using suitable thickening agents and adding them to aqueous/alcoholic compositions of the active compound. Suitable thickening or gelling agents are known in the art, such as the polyvinyl carboxy polymer, Carbomer 940. Ointments and creams may, for example, be formulated with an aqueous or oily base with the addition of suitable thickening and/or gelling agents. Lotions may for example be formulated with an aqueous or oily base, and may also contain one or more emulsifying agents, stabilising agents, dispersing agents, suspending agents, thickening agents, or colouring agents.

Formulations suitable for topical administration may also include solutions or suspensions that may be administered topically in the form of a bath or soak solution or a spray. These formulations may be suitably applied to combat skin irritations, insect bites and foot wounds.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions may for example be applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the active ingredient may be encapsulated with cyclodextrins, or formulated with agents expected to enhance delivery and retention in the nasal mucosa.

Administration to the respiratory tract may also be achieved, for example by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, a fluorohydrocarbon, carbon dioxide, or other suitable gas. The aerosol may conveniently also contain a surfactant such as lecithin. The dose of drug may be controlled by provision of a metered valve.

Alternatively, the active ingredient may for example be provided in the form of a dry powder, for example a powder mix of the compound in a suitable powder base such as lactose, starch, starch derivatives such as hydroxypropylmethyl cellulose and polyvinylpyrrolidone (PVP).

Conveniently, in some embodiments, the powder carrier may form a gel in the nasal cavity. The powder composition may for example be presented in unit dose form, such as in capsules or cartridges of, e.g. gelatin, or blister packs from which the powder may be administered by means of an inhaler.

In formulations intended for administration to the respiratory tract, including intranasal formulations, the active ingredient may for example be provided having a small average particle size, for example of the order of 1 to 10 microns or less. Such a particle size may be obtained by means known in the art, for example by micronization.

Techniques and compositions for making dosage forms as described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004). Pharmaceutical formulation techniques may also be used such as, for example, those disclosed in *Remington's The Science and Practice of Pharmacy,* $23^{rd}$ Ed., Elsevier (2020), or *Remington's Pharmaceutical Sciences,* $21^{st}$ Edition, Mack Publishing, 2005. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332. The contents of each of the aforementioned documents are incorporated herein by reference in their entirety.

Crystalline forms and compositions described herein may be provided in an appropriate container, and labelled for treatment of an indicated condition.

As discussed below, crystalline Form A of the methanesulfonate salt of the compound of formula (I) may be administered in combination with a further active agent. In some embodiments, the pharmaceutical composition comprising crystalline form A also contains a further therapeutic agent.

Therapeutic Methods and Uses

As discussed herein, ATH434 (the compound of formula (I)) has been proposed for use in the treatment of neurodegenerative conditions, such as multiple system atrophy and Parkinson's disease. Accordingly, the crystalline form of the present disclosure finds use in therapy of such conditions.

In another aspect, there is provided crystalline Form A of the methanesulfonate salt of the compound of formula (I), for use in therapy.

In another aspect, there is provided a method of treating, preventing and/or reducing one or more symptoms of a neurological condition in a subject, comprising administering a therapeutically effective amount of crystalline Form A as defined herein, or of a pharmaceutical composition as defined herein, to the subject.

In another aspect, there is provided use of crystalline Form A as defined herein in the manufacture of a medicament for the treatment, prevention and/or reduction of one or more symptoms of a neurological disorder.

In another aspect, there is provided crystalline Form A as defined herein, or a pharmaceutical composition as defined herein, for use in treating, preventing and/or reducing one or more symptoms of a neurological disorder.

In another aspect, there is provided a method of treating, preventing and/or reducing one or more symptoms of a neurological condition in a subject, comprising administering a therapeutically effective amount of the methanesulfonate salt of the compound of formula (I), or of a pharmaceutical composition comprising the methanesulfonate salt of the compound of formula (I), to the subject.

In another aspect, there is provided use of the methanesulfonate salt of the compound of formula (I) in the manufacture of a medicament for the treatment, prevention and/or reduction of one or more symptoms of a neurological disorder.

In another aspect, there is provided the methanesulfonate salt of the compound of formula (I), or a pharmaceutical composition comprising the methanesulfonate salt of the compound of formula (I), for use in treating, preventing and/or reducing one or more symptoms of a neurological disorder.

In some embodiments, the neurodegenerative disease or disorder is selected from the group consisting of Alzheimer's disease, amyotrophic lateral sclerosis, Parkinson's disease, Creutzfeldt-Jacob disease and its variant associated with "mad cow" disease, Huntington's disease, dementia with Lewy body formation, multiple system atrophy, Hallerboden-Spatz disease, diffuse Lewy body disease, fatal familial insomnia, Gertsmann Straussler Sheinker disease, hereditary cerebral haemorrhage with amyloidosis-Dutch type, multiple sclerosis, tauopathies, motor neuron disease and prion diseases.

In some embodiments, the neurodegenerative disease or disorder is selected from the group consisting of multiple system atrophy and Parkinson's disease.

In some embodiments, the disease or disorder is multiple system atrophy.

In some embodiments, the disease or disorder is Parkinson's disease.

Any suitable route of administration may be employed for providing a human or non-human patient with the crystalline form of the present disclosure, or of the pharmaceutical composition comprising the crystalline form. For example, oral, topical, rectal, parenteral, sublingual, buccal, intravenous, intraarticular, intra-muscular, intra-dermal, subcutaneous, inhalational, intraocular, intraperitoneal, intracerebroventricular, transdermal administration and the like may be employed.

The subject to be treated may be any subject, including mammals, birds, fish and reptiles. In some embodiments, the subject is a human, a companion animal, a laboratory animal, a farming or working animal, a farmed bird, a racing animal or a captive wild animal such as those kept in zoos. Examples of suitable subjects include but are not limited to humans, dogs, cats, rabbits, hamsters, guinea pigs, mice, rats, horses, cattle, sheep, goats, deer, pigs, monkeys, marsupials, chickens, geese, canaries, budgies, crocodiles, snakes, lizards and the like. In particular embodiments, the subject is a mammalian subject such as a human, dog, cat, horse, cattle, sheep, goat, pig, deer, rat, guinea pig, kangaroo, rabbit or mouse.

In some embodiments, the subject is a human. In some embodiments, the subject is male. In some embodiments, the subject is female. In some embodiments, the subject is adult. In some embodiments, the subject is a child.

In some other embodiments, the subject is not a human, for example it may be a non-human animal, or a non-human mammal.

An "effective amount" means an amount necessary at least partly to attain the desired response. The amount varies depending upon the health and physical condition of the individual to be treated, the taxonomic group of individual to be treated, the formulation of the composition, the assessment of the medical situation, and other relevant factors.

In some embodiments, the crystalline Form A of the compound of formula (I) is administered in combination with a further therapeutic agent, for example another therapeutic agent which is useful for preventing, treating and/or reducing the symptoms of a neurological condition, for example a neurodegenerative disease or disorder.

In some embodiments, the further therapeutic agent is one which is useful for preventing, treating and/or reducing the symptoms of a neurodegenerative disease or disorder selected from the group consisting of Alzheimer's disease, amyotrophic lateral sclerosis, Parkinson's disease, Creutzfeldt-Jacob disease and its variant associated with "mad cow" disease, Huntington's disease, dementia with Lewy body formation, multiple system atrophy, Hallerboden-Spatz disease, diffuse Lewy body disease, fatal familial insomnia, Gertsmann Straussler Sheinker disease, hereditary cerebral haemorrhage with amyloidosis-Dutch type, multiple sclerosis, tauopathies, motor neuron disease and prion diseases.

In some embodiments, the further therapeutic agent is one which is useful for preventing, treating and/or reducing the symptoms of a neurodegenerative disease or disorder selected from the group consisting of multiple system atrophy and Parkinson's disease. For example, in some embodiments, the further therapeutic agent may be an antibody against aggregated or oligomeric α-synuclein, or a small molecule with the same or similar therapeutic activity.

The crystalline Form A of the methanesulfonate salt of the compound of formula (I) may for example be administered separately to, simultaneously with, or sequentially to the further therapeutic agent.

Those skilled in the art will appreciate that the disclosure herein is susceptible to variations and modifications other than those specifically described. It is to be understood that the disclosure includes all such variations and modifications.

The present disclosure is further described with reference to the following Examples which illustrate some preferred embodiments. However, it is to be understood that the particularity of the following description is not to supersede the generality of the preceding description.

EXAMPLES

Analytical Procedures

X Ray Powder Diffraction

X-Ray power diffraction patterns were collected in accordance with one of the following:

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically, the sample would be exposed to the X-ray beam for 120 seconds. The software used for data collection was GADDS for XP/2000 4.1.43 and the data were analysed and presented using Diffrac Plus EVA v15.0.0.0.

Ambient Conditions

Samples run under ambient conditions were prepared as flat plate specimens using powder as received without grinding. Approximately 1-2 mg of the sample was lightly pressed on a glass slide to obtain a flat surface.

Non-Ambient Conditions

Samples run under non-ambient conditions were mounted on a silicon wafer with heat-conducting compound. The sample was then heated to the appropriate temperature at 20° C./min and subsequently held isothermally for 1 minute before data collection was initiated.

Bruker AXS D8 Advance

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:

Angular range: 2 to 42° 2θ

Step size: 0.05° 2θ

Collection time: 0.5 s/step

PANalytical.

XRPD diffractograms were acquired on PANalytical X'Pert Pro diffractometer using Ni-filtered Cu Kα (45 kV/40 mA) radiation and a step size of 0.03° 2θ and X'celerator™ RTMS (Real Time Multi-Strip) detector. Configuration on the incidental beam side: variable divergence slits (10 mm irradiated length), 0.04 rad Soller slits, fixed anti-scatter slit (0.50°), and 10 mm beam mask. Configuration on the diffracted beam side: variable anti-scatter slit (10 mm observed length) and 0.04 rad Soller slits. Samples were mounted flat on zero-background Si wafers.

Rigaku SmartLab X-Ray Diffractometer

A Rigaku SmartLab X-Ray Diffractometer was configured in Bragg-Brentano reflection or horizontal transmission geometry. A beam stop and knife edge to reduce incident beam and air scatter were used in reflection mode. Data collection parameters are shown in the Table below.

| Parameter | Value | Parameter | Value |
|---|---|---|---|
| Geometry | Bragg-Brentano | Receiving Slit 1 (mm) | 18 |
| Tube Anode | Cu | Receiving Slit 2 (mm) | 20.1/Open |
| Tube Type | Long Fine Focus | Start Angle 2θ (°) | 2/3 |
| Tube Voltage (kV) | 40 | End Angle 2θ (°) | 40 |
| Tube Current (mA) | 44/50 | Step Size (°) | 0.02 |
| Detector | HyPix-3000/DteX250 | Scan Speed (°/min) | 6/2 |
| Monochromator | Ni foil Cu Kβ Filter/None | Spinning (rpm) | 11 |
| Incident Slit (°) | 1/3 | Sample Holder | Low-background Si/Transmission holder with Etnom films |

Proton Nuclear Magnetic Resonance ($^1H$ NMR)

The $^1H$ NMR spectra were collected using either an Agilent DD2 500 MHz spectrometer, or a Bruker 400 MHz instrument. Samples were dissolved in $d_6$-DMSO unless otherwise stated.

Gravimetric Vapor Sorption (GVS)

Sorption isotherms were obtained using a SMS DVS Intrinsic moisture sorption analyser, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 mL/min The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically, 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was carried out using Microsoft Excel using DVS Analysis Suite v6.2 (or 6.1 or 6.0).

Method for SMS DVS Intrinsic Experiments

| Parameter | Value |
|---|---|
| Adsorption-Scan 1 | 40-90 |
| Desorption/ Adsorption-Scan 2 | 90-0, 0-40 |
| Intervals (% RH) | 10 |
| Number of Scans | 2 |
| Flow rate (mL/min) | 200 |
| Temperature (° C.) | 25 |
| Stability (° C./min) | 0.2 |
| Sorption Time (hours) | 6 hour time out |

The sample was recovered after completion of the isotherm and re-analysed by XRPD.

Slurry (SL)

Suspensions were prepared by adding enough solids to a given solvent at the stated conditions so that undissolved solids were present. The mixture was then agitated (typically by stirring) in a sealed vial at the stated temperature for an extended period of time.

Polarized-Light Microscopy (PLM)

The photomicrographs were collected either using Olympus BX60 polarized-light microscope equipped with Olympus DP70 camera, or with a Leica LM/DM polarised light microscope with a digital video camera for image capture.

Typically, a small amount of each sample was placed on a glass slide, mounted in immersion oil and covered with a glass slip, the individual particles being separated as well as possible. The sample was viewed with appropriate magnification and partially polarised light, coupled to a X false-colour filter.

Differential Scanning Calorimetry (DSC)

DSC data were collected on a TA Instruments Discovery DSC equipped with a 50-position auto-sampler. The calibration for thermal capacity was carried out using sapphire and the calibration for energy and temperature was carried out using certified indium. Typically, 0.5-3 mg of each sample, in a pin-holed aluminium pan, was heated at 10° C./min from 25° C. to 300° C. A purge of dry nitrogen at 50 mL/min was maintained over the sample.

The instrument control and data analysis software used was TRIOS v3.2.0.3877.

Thermogravimetric Analysis (TGA)

TGA data were collected on a TA Instruments Discovery TGA, equipped with a 25 position auto-sampler. The instrument was temperature calibrated using certified alumel and nickel. Typically 5-10 mg of each sample was loaded onto a pre-tared aluminium DSC pan and heated at 10° C./min from ambient temperature to 350° C. A nitrogen purge at 25 mL/min was maintained over the sample.

The instrument control and data analysis software used was TRIOS v3.2.0.3877.

Example 1: Synthesis of ATH434 Bromide Salt

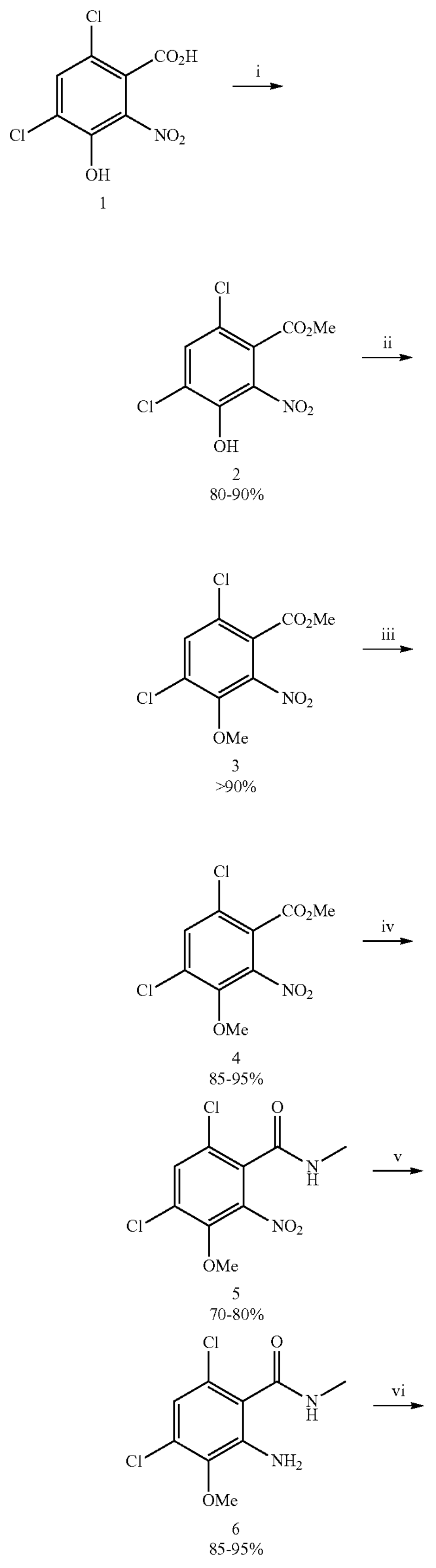

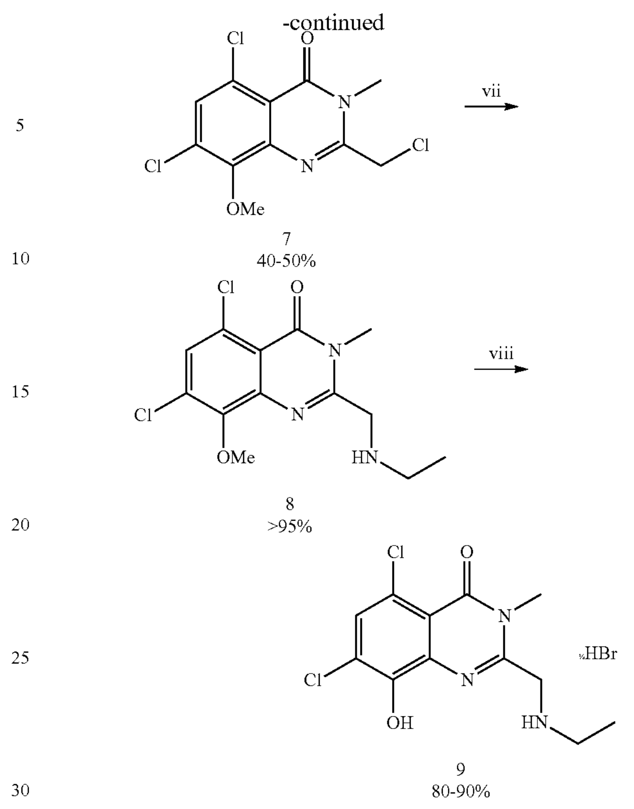

Scheme 1: Synthesis of ATH434 Bromide Salt from Nitro-Benzoic Acid 1 i) MeI, $K_2CO_3$, DMF 65° C.; ii) MeI, $K_2CO_3$, acetone reflux; iii) 2N NaOH, MeOH 60° C.; iv) 1.$SOCl_2$ reflux, 2. 8.0M $MeNH_2$, $CH_2Cl_2$ rt.; v) Fe powder, AcOH 80° C.; vi) $ClCH_2COCl$, AcOH 90° C.; vii) $EtNH_2$, THE rt.; viii) 48% HBr 120° C.

Methyl 4,6-dichloro-3-hydroxy-2-nitrobenzoate (2)

Benzoic acid 1 (25.0 g, 99.2 mmol, U.S. Pat. No. 8,084,459) was dissolved in anhydrous DMF (250 mL), to which $K_2CO_3$ (20.6 g, 149.0 mmol) and MeI (35.2 g, 248.0 mmol) were added, and the resulting mixture heated at 65° C. with stirring under an argon atmosphere for 16 hours. Upon cooling the reaction was concentrated and then acidified to pH 0-2 with conc. HCl. The reaction was then diluted with $H_2O$ (250 mL) and extracted with EtOAc (4×150 mL). The combined organic extracts were washed with brine (2×200 mL), dried ($Na_2SO_4$), filtered and concentrated to afford the title compound as a reddish-brown gummy solid (28.56 g, crude yield—DMF present). $^1H$ NMR (500 MHz, $d_6$-DMSO): δ 3.82 (s, 3H), 8.05 (s, 1H).

Methyl 4,6-dichloro-3-methoxy-2-nitrobenzoate (3)

The methyl ester 2 (28.5 g crude, 107.1 mmol) was dissolved in acetone (250 mL) to which $K_2CO_3$ (22.2 g, 160.7 mmol) and MeI (45.6 g, 321.3 mmol) were added, and the resulting mixture stirred at reflux under an argon atmosphere for 24 hours. Upon cooling the reaction was concentrated and taken up with $H_2O$ (200 mL), then extracted with $CH_2Cl_2$ (3×200 mL). The combined organic extracts were washed with brine (2×200 mL), dried ($Na_2SO_4$), filtered and concentrated to yield the dimethylated compound as a clear brown oil (26.92 g, 97% —some DMF still present). $^1$H NMR (500 MHz, $d_6$-DMSO): δ 3.86 (s, 3H), 3.95 (s, 3H), 8.25 (s, 1H).

4,6-Dichloro-3-methoxy-2-nitrobenzoic acid (4)

The dimethylated compound 3 (26.8 g, 95.7 mmol) was heated at 60° C. in 2N NaOH (150 mL) and MeOH (200 mL) for 3 hours. Upon cooling the MeOH was removed in vacuo leaving an aqueous solution which was extracted with EtOAc (200 mL) to remove organic impurities. The aqueous layer was then acidified with conc. HCl and extracted with EtOAc (3×200 mL). The organic extracts were washed with brine (200 mL), dried ($Na_2SO_4$), filtered and concentrated to afford the benzoic acid as a light yellow solid (23.3 g, 91%). $^1$H NMR (500 MHz, $d_6$-DMSO): δ 3.94 (s, 3H), 8.15 (s, 1H).

4,6-Dichloro-3-methoxy-N-methyl-2-nitrobenzamide (5)

Compound 4 (23.2 g, 87.2 mmol) was heated at reflux in neat $SOCl_2$ (150 mL) for 1 hour. The excess $SOCl_2$ was then distilled off under reduced pressure. Residual $SOCl_2$ was further removed by azeotropic distillation with toluene leaving a red oil which readily crystallised on standing. The acid chloride was dissolved in anhydrous $CH_2Cl_2$ (150 mL) and cooled to 0° C., upon which an 8.0M solution of $MeNH_2$ in EtOH (50 mL 400 mmol) was added dropwise, and the reaction stirred under an argon atmosphere for 20 hours at ambient temperature. The reaction mixture was then concentrated, partitioned between $H_2O$ (200 mL) and EtOAc (200 mL), and then further extracted with EtOAc (2×200 mL). The organic extracts were washed with brine (200 mL), dried ($Na_2SO_4$), filtered and concentrated to afford the amide as a highly crystalline brown solid (17.3 g, 71%). $^1$H NMR (500 MHz, $d_6$-DMSO): δ 2.74 (d, J=4.5 Hz, 3H) 3.94 (s, 3H), 8.17 (s, 1H), 8.83 (d, J=4.5 Hz, 1H).

2-Amino-4,6-dichloro-3-methoxy-N-methylbenzamide (6)

To a suspension of the nitro compound 5 (17.2 g, 61.6 mmol) in glacial AcOH (200 mL) was added Fe powder (15 g, 269 mmol), and the resulting mixture was heated at 80° C. for 1.5 hours. The reaction was then filtered hot through a small pad of celite, which was washed through with EtOAc and a further small amount of AcOH. The filtrate was concentrated and the brown residue taken up in EtOAc (250 mL) and sat. $NaHCO_3$ soln. (250 mL) resulting in a significant emulsion. Upon settling, the aqueous layer was extracted with again with EtOAc (3×200 mL). The organic extracts were washed with brine (300 mL), dried ($Na_2SO_4$), filtered and concentrated to afford the yield the aniline 6 as a tan coloured solid (14.4 g, 94%). $^1$H NMR (500 MHz, $d_6$-DMSO): δ 2.73 (d, J=4.5 Hz, 3H) 3.67 (s, 3H), 5.32 (s, 2H), 6.72 (s, 1H), 8.34 (d, J=4.5 Hz, 1H).

5,7-Dichloro-2-(chloromethyl)-8-methoxy-3-methylquinazolin-4(3H)-one (7)

The aniline derivative 6 (14.4 g, 57.8 mmol) was dissolved in glacial AcOH (150 mL), to which chloroacetyl chloride (18.4 mL, 231 mmol) was added. The resulting solution was added stirred at 90° C. for 2.5 hours. After cooling, the volume of solvent was reduced, and then 2N NaOH was added until the pH was ~6. The mixture was extracted with $CH_2Cl_2$ (3×200 mL), and then the extracts were washed with brine (200 mL), dried ($Na_2SO_4$), filtered and concentrated. The solid residue was then purified by flash chromatography eluting with 20-40% EtOAc/hexanes to afford the desired cyclised material as a light orange solid (8.31 g, 47%). $^1$H NMR (500 MHz, $d_6$-DMSO): δ 3.54 (s, 3H), 4.00 (s, 3H), 4.91 (s, 2H), 7.69 (s, 1H).

5,7-Dichloro-2-((ethylamino)methyl)-8-methoxy-3-methylquinazolin-4(3H)-one (8)

A solution of the cyclised material 7 (8.2 g, 26.7 mmol) in anhydrous THE (100 mL) was cooled to 0° C. and stirred under an atmosphere of argon. At this point a 2.0M solution of $EtNH_2$ in THF (53 mL, 106 mmol) was added dropwise, and then the resulting mixture was allowed to warm to room temperature, followed by further stirring for 1 hour. The reaction was concentrated and taken up into $CH_2Cl_2$ (200 mL) and $H_2O$ (200 mL), and the aqueous layer extracted with $CH_2Cl_2$ (2×200 mL). The organic extracts were washed with brine (200 mL), dried ($Na_2SO_4$), filtered and then concentrated to yield the free amine as an orange solid (8.40 g, 99%). $^1$H NMR (500 MHz, $d_6$-DMSO): δ 1.05 (t, J=7.5 Hz, 3H), 2.40 (br s, 1H), 2.65 (q, J=7.5 Hz, 2H), 3.49 (s, 3H), 3.86 (s, 2H), 3.98 (s, 3H), 7.60 (s, 1H).

5,7-Dichloro-2-((ethylamino)methyl)-8-hydroxy-3-methylquinazolin-4(3H)-one hydrobromide (9)

The methyl ether 8 (8.3 g, 26.3 mmol) was heated at 120° C. in 48% aqueous HBr (120 mL) for 3 hours. The HBr was then distilled off under reduced pressure, and then a small amount of MeOH (20 mL) was added to the residue and concentrated in vacuo. A further amount of MeOH (40 mL) was added to the residue resulting in a brown suspension which was sonicated and left to stand for 15 minutes. The solid material was then filtered and carefully washed with a minimum amount of MeOH (×4), leaving behind 9 as a fluffy light brown powder (8.5 g, 85%). $^1$H NMR (500 MHz, $d_6$-DMSO): δ 1.32 (t, J=7.5 Hz, 3H), 3.16 (q, J=7.5 Hz, 2H), 3.44 (s, 3H), 4.57 (s, 2H), 7.62 (s, 1H), 9.06 (br s, 2H), 10.24 (s, 1H); $^{13}$C NMR (125 MHz, $d_6$-DMSO): d 10.9, 29.5, 42.7, 6.7, 115.6, 121.5, 122.1, 129.4, 136.9, 147.5, 151.3, 158.4. HPLC $t_R$=8.53 min (>98%).

Example 2: Properties of ATH434 Bromide Salt

Solid Forms

Multiple solid forms of ATH434 Bromide salt have been identified. Form 1 was obtained by slurry washing with methyl tert-butyl ether. Following cooling recrystallisation from a 1:1 mixture of methanol and water, a mixture of Form 1 with another polymorph (Form 2) was obtained. Form 2 has not been isolated by itself.

GVS (Gravimetric Vapor Sorption) studies with ATH434 Bromide salt showed the material to be hygroscopic, particularly under high humidity conditions, with a possible hydrate form being obtained. This presents a challenge to its use.

Studies indicate that ATH434 Bromide salt has non-stoichiometric counterion content.

DSC (Differential Scanning Calorimetry) studies indicate unusual events occurring at relatively low temperature.

The material exhibits complex thermal behaviour, suggestive of the existence of further forms of this salt.

Taste

ATH434 Bromide salt was also found to have a bitter taste.

Animal Studies

Consequences of ATH434 administration as the HBr salt have been demonstrated in rats and monkeys.

Rats: In a 28-day study of ATH434 HBr in male rats, doses equal to or greater than 80 mg/kg/day were associated with increased circulating chloride of 2-6% relative to vehicle control; these elevated readings may have simply reflected the combination of circulating chloride and bromide. The elevated chloride values partially reversed after a 14-day recovery period. Administration of ATH434 HBr at 375 mg/kg was associated with adverse, minimal, and diffuse follicular cellular hypertrophy of the thyroid that reversed after 14 days of recovery.

Monkeys: In a short-term study in macaques, 5 daily doses of 600 and 1000 mg/kg of ATH434 HBr induced vomiting which was associated with elevated chloride levels and elevated bromide levels as measured with a selective UV assay. The bromide levels required at least 4 weeks after the final ATH434 HBr dose to normalize.

Summary

The above studies indicate that there are significant challenges to use of ATH434 Bromide salt.

Example 3: Investigation of ATH434 Salts

A range of additional salt forms of ATH434 were prepared. An exemplary preparation for the sulfate salt is provided below.

ATH434 Sulfate Salt

ATH434 free base (8.0 g) was suspended in acetonitrile (250 mL). $H_2SO_4$ (1.05 eq as a 1M solution in TIF) was then added portionwise. The resulting slurry was stirred at RT for ca. 60 h. The solid present was then isolated by filtration and washed with acetonitrile (10 mL) before being dried under vacuum for ca. 16 h to give a powdery white solid (8.2 g, 81%).

The table below summarises properties of a range of salt forms of ATH434.

| ATH434 Salt Form | Comments |
|---|---|
| Free base | Exists as crystalline mono-hydrated form. DSC/TGA analysis suggests existence of a second, anhydrous crystalline form. The monohydrate is prone to dehydrating at relatively low temperature (6.7% mass loss RT-125° C.), likely making it challenging to handle. |
| Sulfate salt | Exhibited a high level of hygroscopicity when assessed by GVS, likely presenting a challenge to its use. A form change on scale up was observed. |
| Maleate salt | Significant amounts of residual solvent contained - possibility of solvated species. A form change was observed, from XRPD |
| Oxalate salt | Significant amounts of residual solvent contained - possibility of solvated species |
| Salicylate salt | Significant amounts of residual solvent contained - possibility of solvated species. A form change was observed, from XRPD. |
| L-malate salt | Instability to temperature and/or humidity |
| Benzoate salt | Instability to temperature and/or humidity |
| L-tartrate salt | Instability to temperature and/or humidity |
| Citrate salt | Instability to temperature and/or humidity |
| Tosylate salt | Instability to temperature and/or humidity |

Summary:

A range of different salt forms of ATH434 have undesirable properties.

Example 4: Preparation of ATH434 Methanesulfonate Salt Form A

ATH434 Bromide salt (8 g, 20.9 mmoL) was suspended in saturated aqueous $NaHCO_3$ (100 mL) solution. The resulting gluggy suspension was washed with $H_2O$ and methanol, then dried under high vacuum. The resulting free base was then dissolved in methanol (150 mL), then methanesulfonic acid (3 mL) was added dropwise to the solution. Solvent was removed to ⅓ volume. The solution was allowed to cool, and ATH434 Methanesulfonate Salt was collected by filtration, as a white solid.

The product was purified by recrystallization from Methanol/$H_2O$ (15 mL/10 mL) to yield a crystalline solid which was designated Form A. Yield 4.9 grams, 59% overall yield.

$^1$H NMR (500 MHz, $d_6$-DMSO): δ 1.32 (t, J=7.5 Hz, 3H), 2.33 (s, 3H), 3.16 (q, J 7.5 Hz, 2H), 3.45 (s, 3H), 4.54 (s, 2H), 7.66 (s, 1H), 8.93 (br s, 2H), 10.36 (s, 1H); m z 302 $[M+H]^+$.

Figure 2:
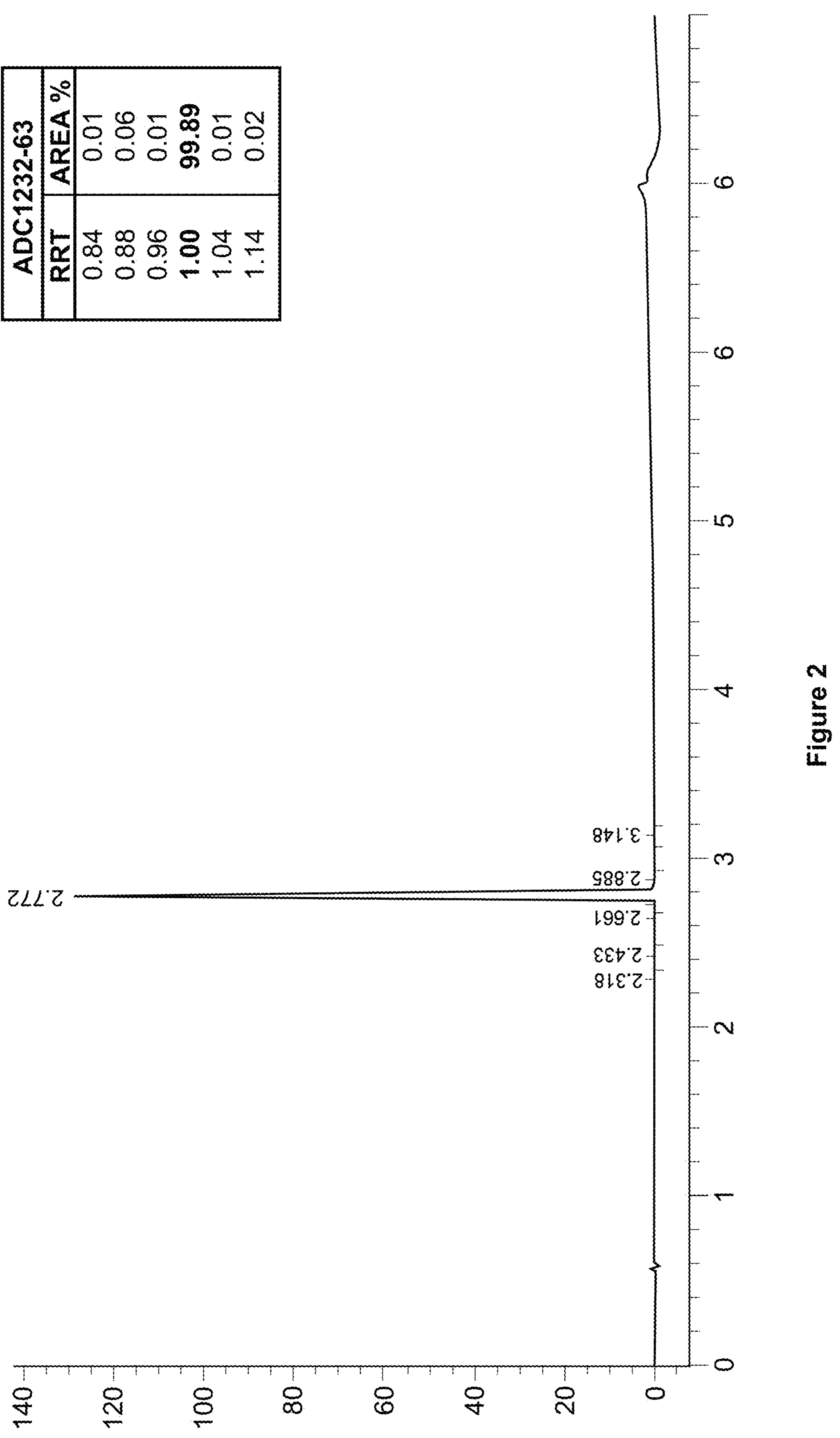
FIG. 2 shows an HPLC chromatogram of a batch of ATH434 methanesulfonate salt Form A.

A representative $^1$H NMR spectrum is shown in FIG. 1, and representative HPLC chromatogram is shown in FIG. 2.

Example 5: Properties of ATH434 Methanesulfonate Salt Form A

Physical Properties

Form A is obtainable as a white crystalline powder.

Form A has a melting point of 291-292° C.

Crystal Habit: Polarized Light Microscopy (PLM)

Figure 3:
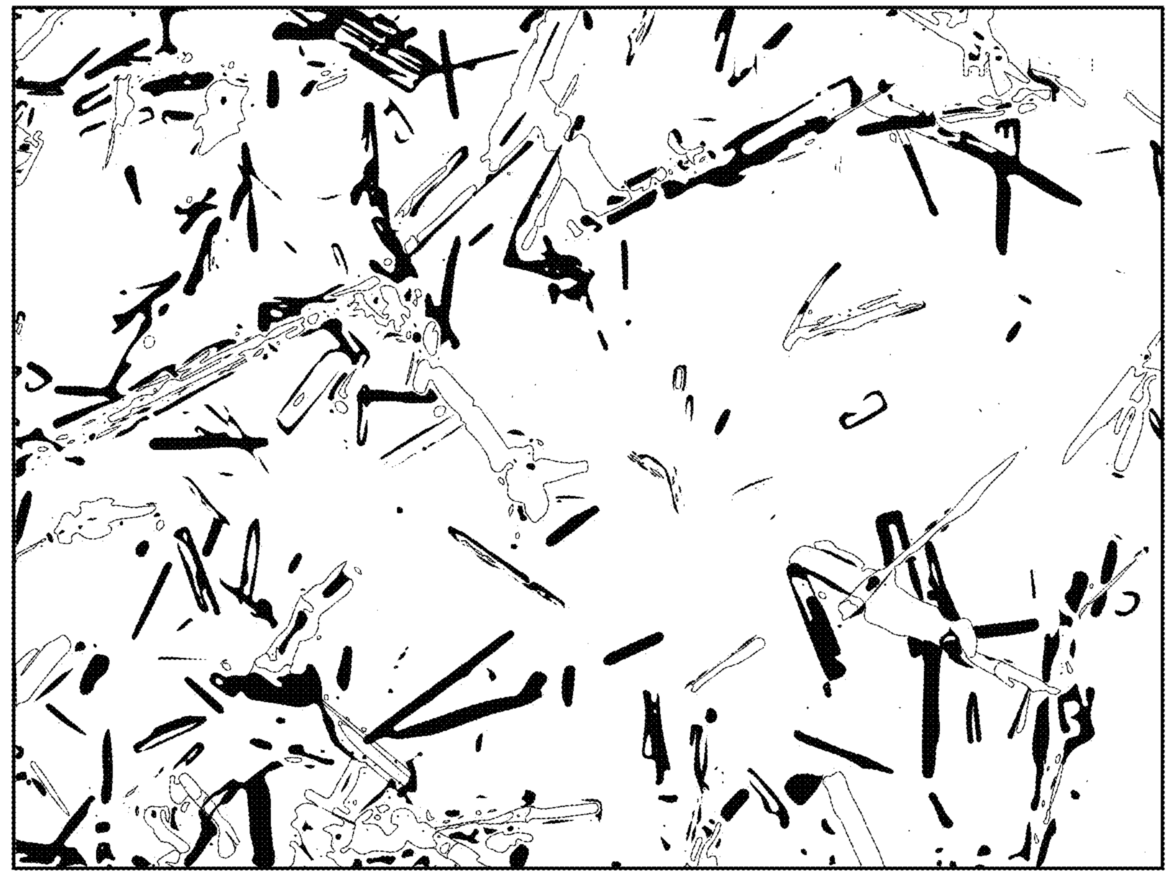
FIG. 3 shows crystals of ATH434 methanesulfonate salt Form A viewed using polarised light microscopy.

PLM analysis showed that Form A of the methanesulfonate salt of ATH434 contains crystals, as shown in FIG. 3.

X-Ray Powder Diffraction (XRPD)

An XRPD diffractogram for a typical batch of crystalline Form A of ATH434 methanesulfonate salt is shown in FIG. 4. A list of 20 peaks and their intensities is listed in the table below. Crystalline Form A was characterized by an X-ray powder diffraction (X-RPD) pattern obtained using the copper wavelengths $\lambda_1$ and $\lambda_2$ of 1.54056 Å and 1.54439 Å showing a crystalline structure and comprising distinctive reflections, expressed as 20 degrees values, at 16.5, 22.4, 22.7, 23.3 and 24.1 degrees 2θ±0.2 2θ, and additionally at 8.4, 10.5, 14.6, 15.1, 15.5, 16.8, 17.3 and 21.4 degrees 2θ±0.2 2θ.

| Position (2θ) | d-value (Å) | Relative Intensity |
|---|---|---|
| 8.4 | 10.55 | 23 |
| 10.5 | 8.43 | 26 |
| 13.3 | 6.65 | 16 |
| 14.6 | 6.06 | 23 |
| 15.1 | 5.85 | 24 |
| 15.5 | 5.70 | 23 |
| 15.9 | 5.56 | 18 |
| 16.5 | 5.38 | 82 |
| 16.8 | 5.29 | 36 |
| 17.3 | 5.14 | 51 |
| 18.4 | 4.82 | 10 |
| 19.0 | 4.66 | 16 |
| 19.3 | 4.61 | 18 |
| 20.3 | 4.38 | 13 |
| 21.1 | 4.22 | 12 |
| 21.4 | 4.15 | 34 |
| 21.7 | 4.09 | 11 |
| 22.0 | 4.04 | 12 |

-continued

| Position (2θ) | d-value (Å) | Relative Intensity |
|---|---|---|
| 22.4 | 3.97 | 67 |
| 22.7 | 3.92 | 100 |
| 23.3 | 3.81 | 34 |
| 24.1 | 3.69 | 48 |
| 24.6 | 3.62 | 14 |
| 25.4 | 3.50 | 19 |

Thermogravimetric Analysis (TGA)/Differential Scanning Calorimetry (DSC)

Figure 5:
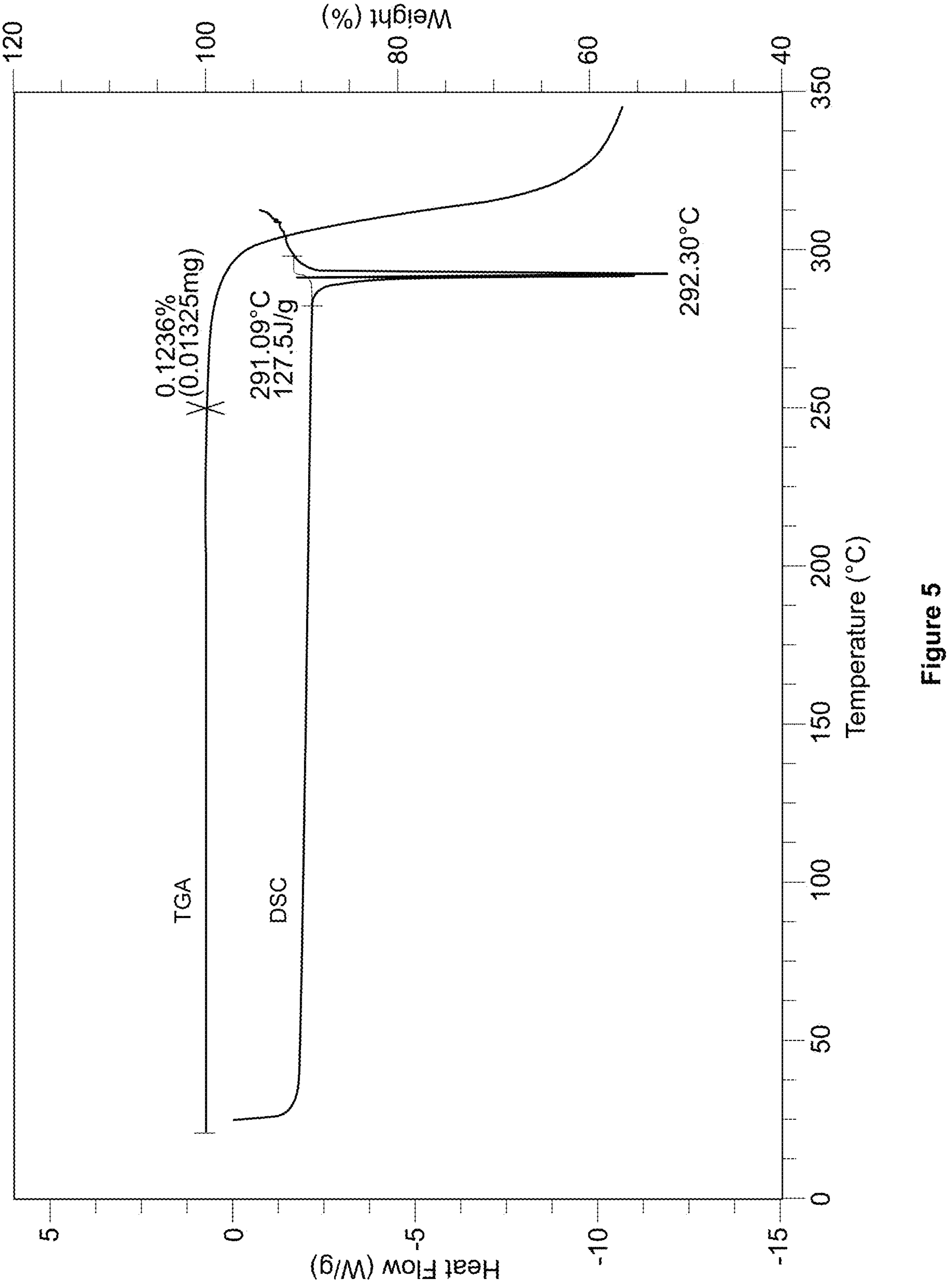
FIG. 5 shows the results of TGA/DSC experiments conducted on a batch of ATH434 methanesulfonate salt Form A.

DSC and TGA analysis was carried out on a typical batch of crystalline Form A of the methanesulfonate salt of ATH434, and the results are shown in FIG. 5. Differential scanning calorimetry (DSC) analysis showed a peak with onset at 291.1° C. and apex at 292.3° C. TGA analysis showed a 0.12% loss of weight on heating up to 250° C. This information supports that crystalline Form A of the methanesulfonate salt of ATH434 is not a solvate.

Gravimetric Vapor Sorption (GVS)

Figure 6:
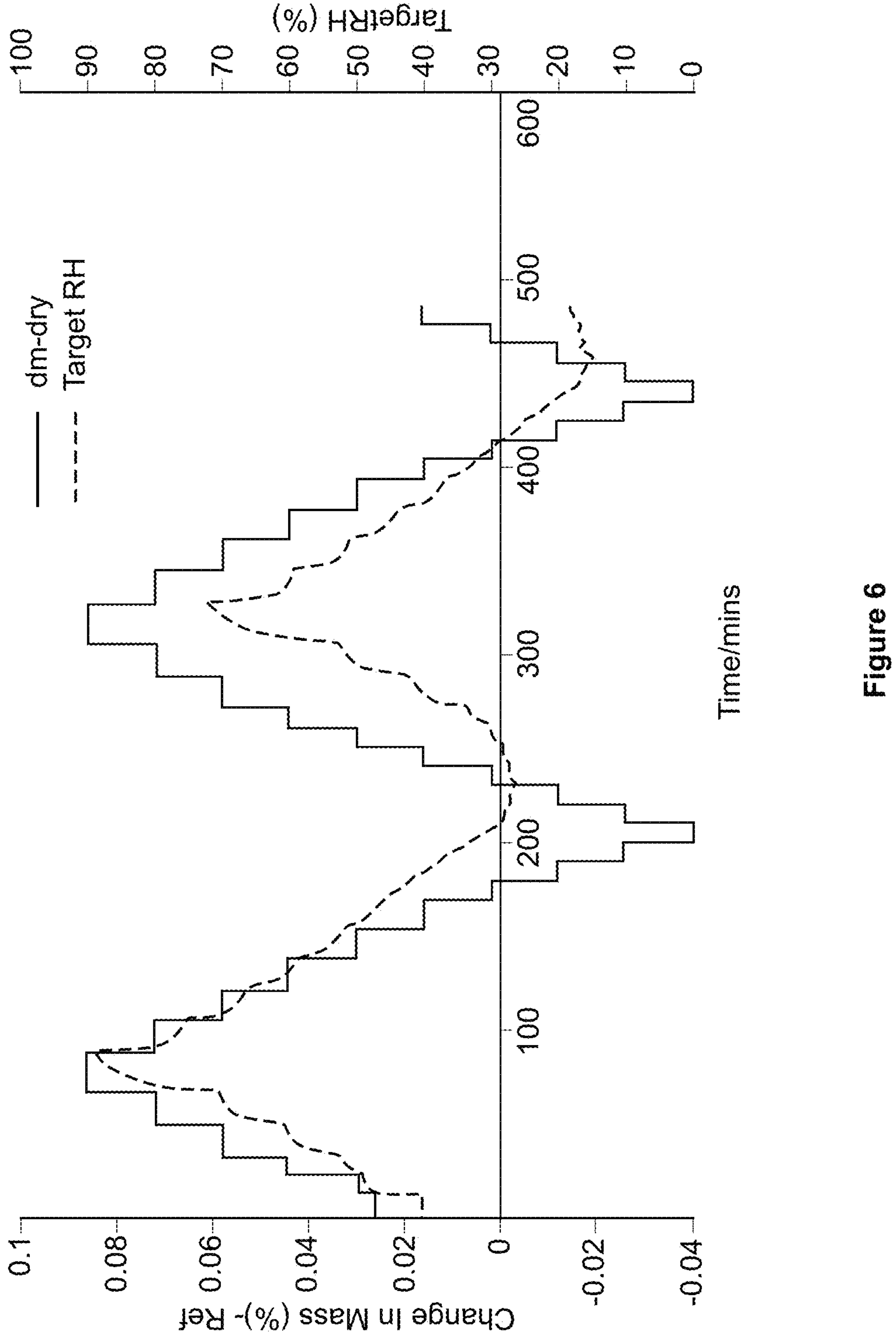
FIG. 6 shows a gravimetric vapor sorption (GVS) profile (i.e. a dynamic vapor sorption mass plot) for a batch of ATH434 methanesulfonate salt Form A, run at 25° C., showing mass and target RH.

A batch of ATH434 methanesulfonate salt Form A was subjected to GVS analysis, as shown in FIG. 6 (dynamic vapor sorption mass plot). There was approximately 0.1% change in mass over 0-90% RH.

Solubility

Form A of the methanesulfonate salt of ATH434 was found to have good solubility properties, having solubility in water at room temperature of 37-55 mg/mL.

The intrinsic dissolution rates of the Form A methanesulfonate salt of ATH434 were also investigated. Dissolution media were aqueous buffers at pH 1, 4.5 and 6.5, representative of gastrointestinal condition. All buffers contained significant levels of chloride ions, either from the buffer itself (0.1 N HCl), or by the addition of sodium chloride to adjust tonicity.

In all three media, the Form A methanesulfonate salt of ATH434 demonstrated rapid initial release, after which the dissolution rate stabilised to a slower rate.

Discs for the intrinsic dissolution evaluation were prepared by weighing approximately 250 mg (in triplicate) and compressing with a small hydraulic press in a 13 mm Wood's die for 3 minutes at a force of approximately 3000 lbs. The surface of each disc was examined carefully to ensure that it was uniform, smooth and free from loose powder.

Dissolution media were prepared at pH 1 (0.1 N HCl), pH 4.5 (21.4 mM acetate buffer/68.6 mM NaCl) and pH 6.5 (21.4 mM phosphate buffer/68.6 mM NaCl).

The dissolution experiments were conducted by attaching the Wood's die containing the disc, to the matching shafts on an Erweka DT6 dissolution apparatus. The discs were lowered into the media (500 mL at 37° C.) and immediately rotated at 100 rpm. Samples of the media (1 mL) were removed prior to immersion of the disc and then at 5, 10, 15, 30, 60 and 120 minutes after the experiment was initiated.

At the end of each experiment, the discs were removed from the media and examined to ensure that the surface of the discs remained uniform and to qualitatively assess the extent of dissolution over the course of the experiment. Media samples were centrifuged (10000 rpm×3 min) and a small aliquot (150 μL) removed, diluted with an equal volume of methanol and stored at 10° C. in preparation for HPLC analysis.

HPLC analysis was conducted on a Waters 2695 HPLC system coupled to a Waters 2998 photo diode array (PDA) detector, analysing at 254 nm. A Phenomenex Luna C18(2) column (5 μm, 50×2 mm i.d.) was used for analysis of all samples, with the column temperature maintained at 25° C. ATH434 was quantified by comparison to a calibration curve over a concentration range of 0.25 to 250 g/mL (calibration standards prepared using ATH434 HBr salt) prepared in 50% aqueous methanol. HPLC analysis was performed using a mobile phase consisting of water, methanol, and 1% aqueous formic acid. Separations were conducted using a flow rate of 0.5 mL/min and an injection volume of 5 L. Processed samples were maintained in the autosampler at a temperature of 10° C. The conditions described led to the elution of ATH434 at 3.8 minutes.

ATH434 standards were prepared from the HBr salt and analysed with each series of triplicate dissolution experiment samples, with correction to the free base concentration for each salt form. Duplicate quality control samples were analysed at the end of each quantitative sample set to ensure system integrity throughout each analysis.

Intrinsic dissolution rates were calculated from the slope of the amount released (g/cm$^2$) versus time (min) profiles. All release profiles are expressed as the ATH434 free base equivalent.

The mesylate salt showed an initial very rapid release by the first time point, the slope was calculated using the period after this initial release. The total percent released over the 120 min period was <15% of the total solid present in all cases thereby fulfilling one of the fundamental assumptions of the intrinsic dissolution rate method.

The intrinsic dissolution rates for the methanesulfonate salt Form A in each medium are shown in Table 2. Dissolution rates reflected the pH dependence of the solubility of ATH434.

Summary of intrinsic dissolution rates for the Form A methanesulfonate salt of ATH434 over a 2 hour period. The results are from the average of triplicate dissolution experiments in each of the media.

| Media | Intrinsic Dissolution Rate (μg ATH434/min/cm$^2$) |
|---|---|
| pH 1 (0.1N HCl) | 122.2 |
| pH 4.5 (Acetate buffer) | 127.4 |
| pH 6.5 (Phosphate buffer) | 15.4 |

Figure 7:
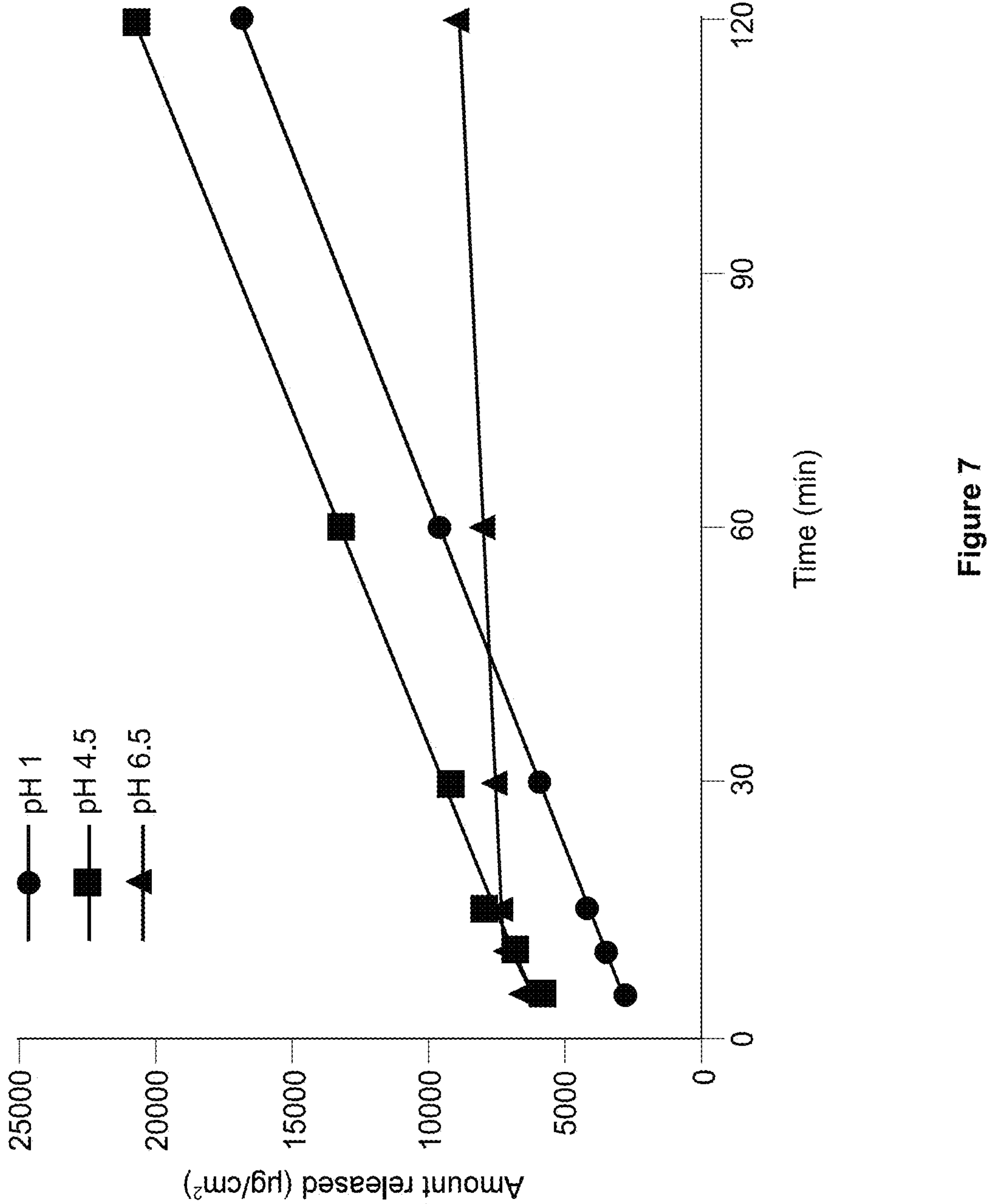
FIG. 7 shows aqueous dissolution profiles for ATH434 methanesulfonate salt Form A at pH 1, pH 4.5 and pH 6.5, expressed as free base equivalent.

The mean dissolution profiles for the Form A methanesulfonate salt in the three test media are presented in FIG. 7. In each case, there was an apparent initial release of ATH434 into the media followed by a steady dissolution rate.

Pharmacokinetic Properties

ATH434 methanesulfonate salt Form A was subjected to pharmacokinetic analysis. ATH434 methanesulfonate salt Form A was orally administered to male Sprague Dawley rats via gavage needle at doses of 3 mg/kg and 30 mg/kg (free base equivalent), at 3 mL/kg per rat for 30 mg/kg dose, and at 0.3 mL/kg per rat for 3 mg/kg group, n=3 rats.

Samples of arterial blood were collected up to 24 h post-dose. Arterial blood was collected directly into borosilicate vials (at 4° C.) containing heparin, Complete® (a protease inhibitor cocktail) and potassium fluoride to minimise potential for ex vivo degradation of compounds in blood/plasma samples. Once collected, blood samples were centrifuged, supernatant plasma was removed and stored frozen (−80° C.) until analysis by LC-MS.

Plasma was collected at the following time intervals: pre-dose, 0.25, 0.5, 1, 2.5, 4, 5, 6, 8, 10, 16 and 24 h post-dose.

Plasma concentration versus time data were analysed using non-compartmental methods (PKSolver Version 2.0). Concentrations below the LLQ were not included in the PK calculations.

ATH434 methanesulfonate salt Form A demonstrated pharmacokinetic properties appropriate for therapeutic administration.

At 30 mg/kg dosing (3 mL/kg dose volume), observed pharmacokinetic parameters were as follows:

| Parameter | Value |
|---|---|
| Measured dose | 36.2 |
| Apparent t ½ (h) | 2.1 |
| T max | 0.7 |
| C max (uM) | 22.2 |
| C max ng/mL | 6716 |
| AUC 0-16 h (uM*h) | 30.7 |
| AUC 0-16 h (ng*h/mL) | 9262 |
| AUC 0-inf (uM*h) | 30.9 |
| AUC 0-inf (ng*h/mL) | 9327 |
| Dose-Normalised Parameters | |
| Cmax/Dose (uM)/(mg/kg) | 0.61 |
| Cmax/Dose (ng/mL)/(mg/kg) | 186 |
| AUC 0-16 h/Dose (uM*h)/(mg/kg) | 0.85 |
| AUC 0-16 h/Dose (ng*h/mL)/(mg/kg) | 256 |
| AUC 0-inf/Dose (uM*h)/(mg/kg) | 0.85 |
| AUC 0-inf/Dose (ng*h/mL)/(mg/kg) | 258 |

At 3 mg/kg dosing (0.3 mL/kg dose volume), observed pharmacokinetic parameters were as follows:

| Parameter | Value |
|---|---|
| Measured dose | 3.5 |
| Apparent t ½ (h) | 2.5 |
| T max | 0.25 |
| C max (uM) | 1.29 |
| C max ng/mL | 390 |
| AUC 0-16 h (uM*h) | 2.02 |
| AUC 0-16 h (ng*h/mL) | 612 |
| AUC 0-inf (uM*h) | 2.02 |
| AUC 0-inf (ng*h/mL) | 612 |
| Dose-Normalised Parameters | |
| Cmax/Dose (uM)/(mg/kg) | 0.37 |
| Cmax/Dose (ng/mL)/(mg/kg) | 111 |
| AUC 0-16 h/Dose (uM*h)/(mg/kg) | 0.58 |
| AUC 0-16 h/Dose (ng*h/mL)/(mg/kg) | 174 |
| AUC 0-inf/Dose (uM*h)/(mg/kg) | 0.58 |
| AUC 0-inf/Dose (ng*h/mL)/(mg/kg) | 174 |

Example 6: Long Term Stability of ATH1434 Methanesulfonate Salt Form A

Seven different samples of ATH434 methanesulfonate salt Form A, manufactured between 4 to 7 years ago, were tested for long term stability. Four of these samples were drug substances (DS), and the remaining three were drug product (DP) tablets which had been stored at 40° C./75% RH since 2020/2021 (see Table below). All samples were analyzed by PXRD in transmission mode, to limit any preferred orientation (P0) effects that might exist. All the samples were consistently found to match the calculated pattern for Form A, with the presence of additional PXRD peaks attributable to mannitol observed in the tablet samples. This suggested no form conversion had taken place over multiple years of storage of the drug substance at room temperature, and of the drug product at 40° C./75% RH.

| Batch No. | Manufacture Date/ Storage Conditions | Sample Description | Result |
|---|---|---|---|
| 1 | May 2018 | Powder, 0.5 g | Form A |
| 2 | September 2018 | Powder, 2.0 g | Form A |
| 3 | March 2018 | Powder, 5.0 g | Form A |
| 4 | March 2020 | Powder, 5.0 g | Form A |
| 5 | February 2020. Stored at 40° C./75% RH since Mar. 12, 2020 | Tablets, 1 bottle. | Form A + mannitol |
| 6 | January 2021. Stored at 40° C./75% RH since Jul. 26, 2021 | Tablets, 24 count | Form A + mannitol |
| 7 | April 2021. Stored at 40° C./75% RH since Sep. 3, 2021 | Tablets, 24 count | Form A + mannitol |

Since no form change was observed, samples were further subjected to process-relevant stressing experiments (see Table below). Samples were slurried in a methanol:water ratio used during the cooling crystallization process, one at sub-ambient (the final isolation temperature) and the other at elevated temperature (the start of the cooling step) for more than a month. Slurries were also set up in pure water at room temperature to investigate for potential hydrates, and in and pure methanol at −15° C. since the crystallization process involved using methanol to wash the wet cake. Two samples were also stressed in the solid-state at 40° C./75% RH and RT/95% RH respectively for more than a month. All slurries were analyzed wet to capture any metastable phases present in equilibrium with the solution. All the above long-term experiments resulted in Form A, confirming no form change under long-term thermodynamic conditions.

| Sample No. | Conditions | Observations | Result |
|---|---|---|---|
| 8 | SL, $H_2O$ (250 μL), RT, 41 days | White solid with clear solvent, analyzed wet | Form A |
| 9 | SL, 60% MeOH in $H_2O$ (0.72 aW, 250 μL), 50° C., 41 days | White solid with clear solvent, analyzed wet | Form A |
| 10 | SL, 60% MeOH in $H_2O$ (0.72 aW, 250 μL), −15° C., 41 days | White slurry, analyzed wet | Form A |
| 11 | SL, MeOH (250 μL), −15° C., 41 days | White slurry, analyzed wet | Form A |
| 12 | Stress at 40° C., 75% RH, 41 days | White slurry, analyzed dry | Form A |
| 13 | Stress at RT, 95% RH, 41 days | White slurry, analyzed dry | Form A |

All attempts used 50 mg of batch rom the previous experiments.

Example 7: Further Preparation of ATH434 Methanesulfonate Salt Form A

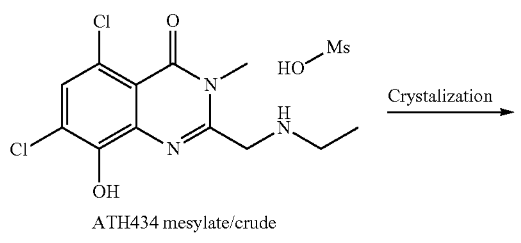

ATH434 mesylate/crude

-continued

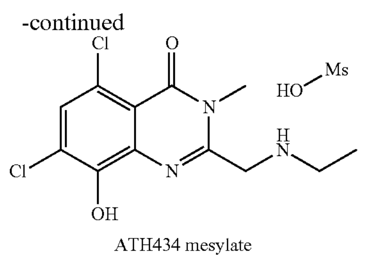

ATH434 mesylate

The following method can be used to prepare ATH434 methanesulfonate salt Form A. Before starting the batch, reflux the reactor with methanol, unload and dry the reactor. Charge methanol (288 mL, 9.6 V) into the reactor at 30±5° C. Charge treated/purified water (192 mL, 6.4 V) into the reactor at 30±5° C. and stir for 10-15 min. Charge ATH434 methanesulfonate salt (30.0 g) into the reactor at 30±5° C. and stir the reaction mass for 10-15 min. Raise the temperature of the solution to 62.5±2.5° C. Stir the mixture for not less than 30 min at 62.5±2.5° C.

Pre-heat the inside clean room reactor by circulating with hot water of temperature 62.5±2.5° C. for 1 hr before receiving the reaction mass. Recirculate the reaction mass through a Candy/leaf filter into the same reactor minimum 15 min. Filter the reaction mass through a Candy/leaf filter followed by a micron filter (transfer to clean room). Use a 0.2 micron filter for filtration. Charge methanol (42.0 mL, 1.4 V) into the reactor (outside clean room) at 30±5° C. Charge treated/purified water (18.0 mL, 0.6V) into the reactor at 30±5° C. and stir for 10-15 min.

Raise the temperature of the solution to 62.5±2.5° C. Heating should be performed by using hot water circulation. Filter the solution through Candy/leaf filter followed by a 0.2 micron filter (transfer to clean room).

Raise the temperature of the solution to 62.5±2.5° C. to get a clear solution and maintain the temperature for 30-60 min. Slowly allow the reaction mass to cool to 43.5±0.3.5° C. in not less than 30 min. Stir the reaction at 43.5±0.3.5° C. for not less than 1 hr.

Slowly cool the reaction mass to 0-5° C. in not less than 3 hr. For cooling initially use RT water then chilled water followed by brine solution. Stir the reaction mass at 0-5° C. for not less than 2 hr.

Filter the solid and wash the wet cake with prechilled (0-5° C.) methanol (60 mL, 2.0V). Filter the methanol through a micron filter before washing and cool to 0-5° C. Suck dry the material for not less than 1 hr.

Dry the wet material under vacuum at not less than 600 mmHg at 30±5° C. for 1-2 hrs. Dry the wet material under vacuum not less than 600 mmHg at 57.5±2.5° C. for 4±1 hrs. Cool the dryer to 30±5° C., release the vacuum with nitrogen and de-lump the material. Dry the material under vacuum NLT 600 mmHg at 57.5±2.5° C. for 5±1 hrs. Cool the dryer to 30±5° C., and release the vacuum with nitrogen. Assay and continue drying if necessary. Unload the dry material and check the weight.

Charge methanol (6.0 V) into the clean room reactor at 30±5° C. Filter the methanol through a micron filter. Charge treated/purified water (4.0 V) into the clean room reactor and stir for 10-15 min at 30±5° C. Filter the treated/purified water through a micron filter. Charge the dry material from above into the clean room reactor at 30±5° C. Raise the temperature of the solution to 50±5° C. Heating should be performed by using hot water circulation. Stir the reaction at 50±5° C. for not less than 2 hr. Slowly cool the reaction mass to 0-5° C. in not less than 3 hr. For cooling initially use RT water then chilled water followed by brine solution. Stir the reaction mass at 0-5° C. for not less than 2 hr. Filter the solid and wash the wet cake with pre-chilled methanol (2.0 V). Filter the methanol through a micron filter before washing and cool to 0-5° C. Suck dry the material for not less than 1 hrs.

Dry the wet material under vacuum at not less than 600 mmHg at 30±5° C. for 1-2 hrs. Dry the wet material under vacuum at not less than 600 mmHg at 57.5±2.5° C. for 4±1 hrs. Cool the dryer to 30±5° C., release the vacuum with nitrogen and de-lump the material. Dry the material under vacuum NLT 600 mmHg at 57.5±2.5° C. for 5±1 hrs. Cool the dryer to 30±5° C., release the vacuum with nitrogen. Assay and continue drying if necessary. Unload the dry material and check the weight.

Yield range: 62.5±22.5%

EMBODIMENTS

The following numbered embodiments are provided herein:

1. A crystalline form (Form A) of the methanesulfonate salt of the compound of formula (I):

(I)

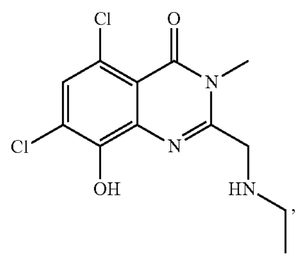

wherein the crystalline form exhibits an X-ray power diffraction pattern comprising peaks at each of 16.5, 22.4, 22.7, 23.3 and 24.1 degrees 2θ±0.2 2θ as measured by X-ray powder diffraction.

2. The crystalline form according to embodiment 1, wherein the crystalline form exhibits an X-ray powder diffraction pattern comprising peaks at one or more of 8.4, 10.5, 14.6, 15.1, 15.5, 16.8, 17.3 and 21.4 degrees 2θ±0.2 2θ as measured by X-ray powder diffraction.

3. The crystalline form according to embodiment 2, wherein the crystalline form exhibits an X-ray powder diffraction pattern comprising peaks at each of 8.4, 10.5, 14.6, 15.1, 15.5, 16.5, 16.8, 17.3, 21.4, 22.4, 22.7, 23.3 and 24.1 degrees 2θ±0.2 2θ as measured by X-ray powder diffraction.

4. The crystalline form according to any of embodiments 1 to 3, wherein the crystalline form exhibits an X-ray powder diffraction pattern substantially as shown in FIG. 4.

5. The crystalline form according to any of embodiments 1 to 4, wherein the crystalline form has a differential scanning calorimetry profile showing an endothermic peak with peak onset at 291° C.±5° C. and peak at 292° C.±5° C.

6. The crystalline form according to any of embodiments 1 to 5, wherein the crystalline form exhibits loss of not more than 0.3% mass during heating to 250° C. when subjected to thermogravimetric analysis.

7. The crystalline form according to any of embodiments 1 to 6, wherein the crystalline form is substantially unsolvated.

8. The crystalline form according to any of embodiments 1 to 7, wherein the methanesulfonate salt of the compound of formula (I) has a purity of at least 98% by mass.
9. Apharmaceutical composition comprising:
   a crystalline form according to any of embodiments 1 to 8; and
   a pharmaceutically acceptable excipient and/or carrier.
10. A method of treating, preventing and/or reducing one or more symptoms of a neurological condition in a subject, comprising administering a therapeutically effective amount of a crystalline form according to any of embodiments 1 to 8, or of a pharmaceutical composition according to embodiment 9, to the subject.
11. Use of a crystalline form according to any of embodiments 1 to 8 in the manufacture of a medicament for the treatment, prevention and/or reduction of one or more symptoms of a neurological disorder.
12. A crystalline form according to any of embodiments 1 to 8, or a pharmaceutical composition according to embodiment 9, for use in treating, preventing and/or reducing one or more symptoms of a neurological disorder.
13. The method, use, crystalline form for use or pharmaceutical composition for use according to any of embodiments 10 to 12, wherein the neurological condition is a neurodegenerative disease or disorder.
14. The method, use, crystalline form for use or pharmaceutical composition for use according to embodiment 13, wherein the neurodegenerative disease or disorder is selected from the group consisting of Alzheimer's disease, amyotrophic lateral sclerosis, Parkinson's disease, Creutzfeldt-Jacob disease and its variant associated with "mad cow" disease, Huntington's disease, dementia with Lewy body formation, multiple system atrophy, Hallerboden-Spatz disease, diffuse Lewy body disease, fatal familial insomnia, Gertsmann Straussler Sheinker disease, hereditary cerebral haemorrhage with amyloidosis-Dutch type, multiple sclerosis, tauopathies, motor neuron disease and prion diseases.
15. The method, use, crystalline form for use or pharmaceutical composition for use according to embodiment 13, wherein the neurodegenerative disease or disorder is selected from the group consisting of multiple system atrophy and Parkinson's disease.
16. A process for producing a crystalline form according to any of embodiments 1 to 8, comprising:
   subjecting the methanesulfonate salt of the compound of formula (I):

(I)

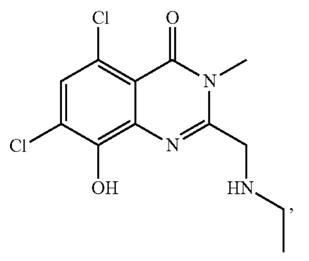

to crystallisation using an alcoholic solvent.
17. The process according to embodiment 16, wherein the alcoholic solvent is a methanolic solvent.
18. The process according to embodiment 17, wherein the alcoholic solvent is aqueous methanol in a methanol: water volume:volume ratio in the range of from 2:1 to 1:1.
19. A method of treating, preventing and/or reducing one or more symptoms of a neurological condition in a subject, comprising administering a therapeutically effective amount of a methanesulfonate salt of a compound of formula (I):

(I)

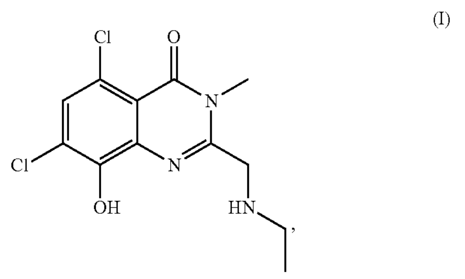 [SMILES: CCNCc1nc2c(O)c(Cl)cc(Cl)c2c(=O)n1C]

or of a pharmaceutical composition comprising a methanesulfonate salt of a compound of formula (I) and a pharmaceutically acceptable excipient and/or carrier, to the subject.
20. Use of a methanesulfonate salt of a compound of formula (I):

(I)

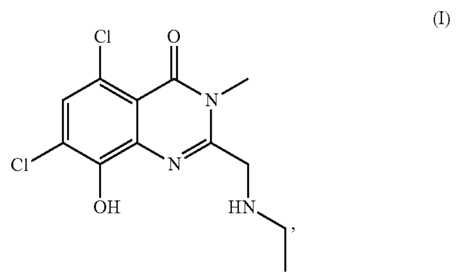 [SMILES: CCNCc1nc2c(O)c(Cl)cc(Cl)c2c(=O)n1C]

for the manufacture of a medicament for the treatment, prevention and/or reduction of one or more symptoms of a neurological disorder.
21. A methanesulfonate salt of a compound of formula (I):

(I)

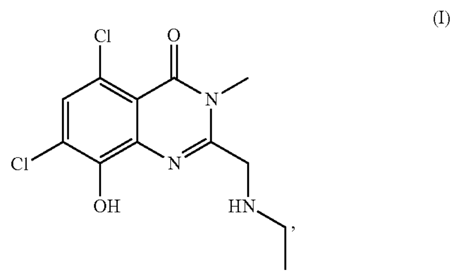 [SMILES: CCNCc1nc2c(O)c(Cl)cc(Cl)c2c(=O)n1C]

or a pharmaceutical composition comprising a methanesulfonate salt of a compound of formula (I) and a pharmaceutically acceptable carrier and/or excipient, for use in treating, preventing and/or reducing one or more symptoms of a neurological disorder.
22. The method, use, methanesulfonate salt of a compound of formula (I) for use, or pharmaceutical composition for use, according to any of embodiments 19 to 21, wherein the neurological condition is a neurodegenerative disease or disorder.

23. The method, use, methanesulfonate salt of a compound of formula (I) for use, or pharmaceutical composition for use, according to embodiment 22, wherein the neurodegenerative disease or disorder is selected from the group consisting of Alzheimer's disease, amyotrophic lateral sclerosis, Parkinsons disease, Creutzfeldt-Jacob disease and its variant associated with "mad cow" disease, Huntington's disease, dementia with Lewy body formation, multiple system atrophy, Hallerboden-Spatz disease, diffuse Lewy body disease, fatal familial insomnia, Gertsmann Straussler Sheinker disease, hereditary cerebral haemorrhage with amyloidosis-Dutch type, multiple sclerosis, tauopathies, motor neuron disease and prion diseases.

24. The method, use, methanesulfonate salt of a compound of formula (I) for use, or pharmaceutical composition for use, according to embodiment 23, wherein the neurodegenerative disease or disorder is selected from the group consisting of multiple system atrophy and Parkinson's disease.

The invention claimed is:

1. A crystalline form of the methanesulfonate salt of the compound of formula (I):

(I)

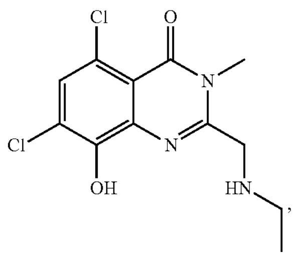

wherein the crystalline form exhibits an X-ray powder diffraction pattern comprising peaks at each of 16.5, 22.4, 22.7, 23.3 and 24.1 degrees 2θ±0.2 2θ as measured by X-ray powder diffraction.

2. The crystalline form as claimed in claim 1, wherein the crystalline form exhibits an X-ray powder diffraction pattern comprising peaks at one or more of 8.4, 10.5, 14.6, 15.1, 15.5, 16.8, 17.3 and 21.4 degrees 2θ±0.2 2θ as measured by X-ray powder diffraction.

3. The crystalline form as claimed in claim 2, wherein the crystalline form exhibits an X-ray powder diffraction pattern comprising peaks at each of 8.4, 10.5, 14.6, 15.1, 15.5, 16.5, 16.8, 17.3, 21.4, 22.4, 22.7, 23.3 and 24.1 degrees 2θ±0.2 2θ as measured by X-ray powder diffraction.

4. The crystalline form as claimed in claim 1, wherein the crystalline form exhibits an X-ray powder diffraction pattern comprising peaks at each of 8.4, 10.5, 13.2, 14.6, 15.1, 15.5, 15.9, 16.5, 16.8, 17.3, 18.4, 19.3, 20.3, 21.4, 22.0, 22.4, 22.7, 23.3, 24.1, 24.6 and 25.4 degrees 2θ±0.2 2θ as measured by X-ray powder diffraction.

5. The crystalline form as claimed in claim 1, wherein the crystalline form has a differential scanning calorimetry profile showing an endothermic peak with peak onset at 291° C.±5° C. and peak at 292° C.±5° C.

6. The crystalline form as claimed in claim 1, wherein the crystalline form has a differential scanning calorimetry profile showing an endothermic peak with peak onset at 291° C.±2° C.

7. The crystalline form as claimed in claim 1, wherein the crystalline form exhibits loss of not more than 0.3% mass during heating to 250° C. when subjected to thermogravimetric analysis.

8. The crystalline form as claimed in claim 1, wherein the crystalline form is unsolvated.

9. The crystalline form as claimed in claim 1, wherein the methanesulfonate salt of the compound of formula (I) has a purity of at least 98% by mass.

10. A pharmaceutical composition comprising:

a crystalline form of the methanesulfonate salt of the compound of formula (I) as claimed in claim 1; and a pharmaceutically acceptable excipient and/or carrier.

11. The pharmaceutical composition of claim 10, wherein at least 90% by mass of the methanesulfonate salt of the compound of formula (I) in the pharmaceutical composition is in the crystalline form.

12. The pharmaceutical composition of claim 10, wherein at least 98% by mass of the methanesulfonate salt of the compound of formula (I) in the pharmaceutical composition is in the crystalline form.

13. The pharmaceutical composition of claim 10, wherein the methanesulfonate salt of the compound of formula (I) has a purity of at least 98% by mass.

14. A method of treating, preventing and/or reducing one or more symptoms of a neurological condition in a subject, comprising administering a therapeutically effective amount of a crystalline form as claimed in claim 1 to the subject.

15. The method as claimed in claim 14, wherein the neurological condition is a neurodegenerative disease or disorder.

16. The method as claimed in claim 15, wherein the neurodegenerative disease or disorder is selected from the group consisting of Alzheimer's disease, amyotrophic lateral sclerosis, Parkinson's disease, Creutzfeldt-Jacob disease and its variant associated with "mad cow" disease, Huntington's disease, dementia with Lewy body formation, multiple system atrophy, Hallerboden-Spatz disease, diffuse Lewy body disease, fatal familial insomnia, Gertsmann Straussler Sheinker disease, hereditary cerebral haemorrhage with amyloidosis-Dutch type, multiple sclerosis, tauopathies, motor neuron disease and prion diseases.

17. The method as claimed in claim 15, wherein the neurodegenerative disease or disorder is selected from the group consisting of multiple system atrophy and Parkinson's disease.

18. A process for producing a crystalline form as claimed in claim 1, comprising:

subjecting the methanesulfonate salt of the compound of formula (I):

(I)

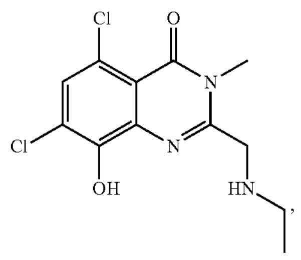

to crystallisation using an alcoholic solvent.

19. The process as claimed in claim 18, wherein the alcoholic solvent is a methanolic solvent.

20. The process as claimed in claim 19, wherein the alcoholic solvent is aqueous methanol in a methanol:water volume:volume ratio in the range of from 2:1 to 1:1.

21. The crystalline form as claimed in claim 3, wherein the crystalline form exhibits an X-ray powder diffraction pattern comprising one or more additional peaks at 13.2, 15.9, 18.4, 19.3, 20.3, 22.0, 24.6 and 25.4 degrees 2θ±0.2 2θ as measured by X-ray powder diffraction.

* * * * *